(12) United States Patent
Chopra et al.

(10) Patent No.: US 8,801,701 B2
(45) Date of Patent: Aug. 12, 2014

(54) METHOD AND APPARATUS FOR OBTAINING QUANTITATIVE TEMPERATURE MEASUREMENTS IN PROSTATE AND OTHER TISSUE UNDERGOING THERMAL THERAPY TREATMENT

(75) Inventors: Rajiv Chopra, Toronto (CA); Michael Bronskill, Toronto (CA); Kee Tang, Mississauga (CA)

(73) Assignee: Sunnybrook Health Sciences Centre, Toronto, ON (CA)

( * ) Notice: Subject to any disclaimer, the term of this patent is extended or adjusted under 35 U.S.C. 154(b) by 1370 days.

(21) Appl. No.: 11/728,778

(22) Filed: Mar. 27, 2007

(65) Prior Publication Data

US 2007/0239062 A1 Oct. 11, 2007

Related U.S. Application Data

(63) Continuation-in-part of application No. 11/076,669, filed on Mar. 9, 2005, now Pat. No. 7,771,418.

(60) Provisional application No. 60/786,537, filed on Mar. 27, 2006.

(51) Int. Cl.
 *A61B 18/10* (2006.01)
(52) U.S. Cl.
 USPC .............................................. 606/27; 607/100
(58) Field of Classification Search
 USPC .................... 607/100–102; 606/27, 32, 34
 See application file for complete search history.

(56) References Cited

U.S. PATENT DOCUMENTS

| | | |
|---|---|---|
| 4,880,011 A | 11/1989 | Imade et al. |
| 5,295,484 A | 3/1994 | Marcus et al. |
| 5,593,381 A | 1/1997 | Tannenbaum et al. |
| 5,593,415 A | 1/1997 | Adrian |
| 5,601,526 A | 2/1997 | Chapelon et al. |
| 5,620,479 A | 4/1997 | Diederich |
| 5,647,361 A | 7/1997 | Damadian |
| 5,666,954 A | 9/1997 | Chapelon et al. |
| 5,733,315 A | 3/1998 | Burdette et al. |
| 6,050,943 A | 4/2000 | Slayton et al. |
| 6,077,257 A | 6/2000 | Edwards et al. |
| 6,100,626 A | 8/2000 | Frey et al. |
| 6,122,551 A | 9/2000 | Rudie et al. |
| 6,159,207 A * | 12/2000 | Yoon ............................... 606/41 |

(Continued)

OTHER PUBLICATIONS

Chopra et al. *Med. Phys.*, 27(6)1281-1286 (2000).

(Continued)

*Primary Examiner* — Michael Peffley
*Assistant Examiner* — Samantha Good
(74) *Attorney, Agent, or Firm* — Intrinsic Law Corp.; Ibrahim M. Hallaj

(57) ABSTRACT

The invention provides a method and apparatus for monitoring a thermal effect of a conformal thermal treatment to diseased tissue in a target volume. The method includes acquiring a reference image of the volume containing the diseased tissue at a first position of the device, determining a baseline temperature distribution of the reference image, acquiring an image of the volume containing the diseased tissue while delivering a treatment to the volume, performing a phase subtraction between the image and the reference image to determine a change in phase between the image and the reference image and determining a current spatial temperature distribution in the volume containing the diseased tissue.

16 Claims, 19 Drawing Sheets

(56) References Cited

U.S. PATENT DOCUMENTS

| | | | |
|---|---|---|---|
| 6,241,725 B1* | 6/2001 | Cosman .................. 606/41 |
| 6,379,320 B1 | 4/2002 | Lafon et al. |
| 6,393,314 B1 | 5/2002 | Watkins et al. |
| 6,418,337 B1 | 7/2002 | Torchia et al. |
| 6,432,067 B1 | 8/2002 | Martin et al. |
| 6,490,488 B1 | 12/2002 | Rudie et al. |
| 6,500,121 B1 | 12/2002 | Stayton et al. |
| 6,516,211 B1 | 2/2003 | Acker et al. |
| 6,522,142 B1 | 2/2003 | Freundlich |
| 6,537,306 B1 | 3/2003 | Burdette et al. |
| 6,542,767 B1 | 4/2003 | McNichols et al. |
| 6,559,644 B2 | 5/2003 | Freundlich et al. |
| 6,566,878 B1* | 5/2003 | Komura et al. ........... 324/315 |
| 6,582,381 B1 | 6/2003 | Yehezkeli et al. |
| 6,589,174 B1 | 7/2003 | Chopra et al. |
| 6,618,608 B1 | 9/2003 | Watkins et al. |
| 6,618,620 B1 | 9/2003 | Freundlich et al. |
| 6,623,430 B1 | 9/2003 | Stayton et al. |
| 6,671,535 B1 | 12/2003 | McNichols et al. |
| 6,692,450 B1 | 2/2004 | Coleman |
| 6,692,518 B2 | 2/2004 | Carson |
| 6,735,461 B2 | 5/2004 | Vitek et al. |
| 6,746,465 B2 | 6/2004 | Diederich et al. |
| 6,755,849 B1 | 6/2004 | Gowda et al. |
| 6,818,012 B2 | 11/2004 | Ellingboe |
| 7,135,029 B2 | 11/2006 | Makin et al. |
| 7,167,741 B2 | 1/2007 | Torchia et al. |
| 7,229,411 B2 | 6/2007 | Stayton et al. |
| 7,233,820 B2 | 6/2007 | Gilboa |
| 7,344,529 B2 | 3/2008 | Torchia et al. |
| 7,404,809 B2 | 7/2008 | Susi |
| 7,473,224 B2 | 1/2009 | Makin |
| 7,771,418 B2 | 8/2010 | Chopra et al. |
| 7,806,892 B2 | 10/2010 | Makin et al. |
| 7,951,182 B2 | 5/2011 | Stelea et al. |
| 7,993,289 B2 | 8/2011 | Quistgaard et al. |
| 8,021,406 B2 | 9/2011 | Cazzini et al. |
| 8,025,688 B2 | 9/2011 | Diederich et al. |
| 8,066,641 B2 | 11/2011 | Barthe et al. |
| 8,244,327 B2 | 8/2012 | Fichtinger et al. |
| 2002/0193682 A1 | 12/2002 | Torchia et al. |
| 2003/0013970 A1 | 1/2003 | Makin |
| 2003/0018266 A1 | 1/2003 | Makin et al. |
| 2003/0018270 A1 | 1/2003 | Makin et al. |
| 2003/0036706 A1 | 2/2003 | Slayton et al. |
| 2003/0040698 A1 | 2/2003 | Makin et al. |
| 2003/0069502 A1 | 4/2003 | Makin et al. |
| 2003/0092988 A1 | 5/2003 | Makin |
| 2004/0039280 A1* | 2/2004 | Wu et al. .................. 600/412 |
| 2004/0044375 A1 | 3/2004 | Diederich et al. |
| 2004/0249261 A1 | 12/2004 | Torchia et al. |
| 2005/0065429 A1* | 3/2005 | Zhou ........................ 600/412 |
| 2008/0242970 A1 | 10/2008 | Minagawa et al. |
| 2009/0143775 A1 | 6/2009 | Rizoiu et al. |
| 2009/0171185 A1 | 7/2009 | Chou et al. |

OTHER PUBLICATIONS

Chopra et al. *IEEE Transactions on Ultrasonics, Ferroelectrics, and Frequency Control*, 50(7):881-889 (2003).
Diederich et al. *Med Phys.*, 31(2);405-413 (2004).
Kowalski et al. *Phys. Med. Biol.*, 48:633-651 (2003).
Lafon et al. *Ultrasonics*, 36:683-687 (1998).
Lafon et al. *Ultrasound Med. Biol.*, 30(1):113-122 (2004).
McNichols et al. *Lasers Surg. Med.*, 34:48-55 (2004).
Ross et al., *Phys. Med. Biol.*, 49:189-204 (2004).
Smith et al. *Int. J. Hyperthermia*, 17(3):271-282 (2001).
Vanne et al. *Phys. Med. Biol.*, 48:31-43 (2003).
Chopra et al., Med. Phys., 27(6): 1281-1286, 2000.
Chopra et al., IEEE Transactions on Ultrasonics, Ferroelectrics, and Frequency Control, 50(7):881-889, 2003.
Diederich et al., Med. Phys., 31(2):405-413, 2004.
Kowalski et al., Phys. Med. Biol., 48:633-651, 2003.
Lafon et al., Ultrasonics, 36:683-687, 1998.
Lafon et al., Ultrasound Med. Biol., 30(1):113-122, 2004.
McNichols et al., Lasers Surg. Med., 34:48-55, 2004.
Ross et al., Phys. Med. Biol., 49:189-204, 2004.
Smith et al., Int. J. Hyperthermia, 17(3): 271-282, 2001.
Vanne et al., Phys. Med. Biol., 48: 31-43, 2003.

* cited by examiner

METHOD AND APPARATUS FOR OBTAINING QUANTITATIVE TEMPERATURE MEASUREMENTS IN PROSTATE AND OTHER TISSUE UNDERGOING THERMAL THERAPY TREATMENT

RELATED APPLICATIONS

This application is a continuation-in-part of U.S. patent application Ser. No. 11/076,669, now U.S. Pat. No. 7,771,418, filed Mar. 9, 2005, which is incorporated herein by reference, and also claims the benefit of priority to U.S. Provisional Application Ser. No. 60/786,537, filed Mar. 27, 2006 and entitled, "Method for Obtaining Quantitative Temperature Measurements Non-Invasively In Prostate Tissue," which is also incorporated herein by reference.

TECHNICAL FIELD

The present invention relates to treatment of various medical conditions using thermal therapy. Various aspects include interstitial, intracavitary or external sources of energy for treatment of various diseases including tumors, benign prostatic hyperplasia, and in particular, prostate cancer. More specifically, embodiments of the present invention relate to obtaining accurate, quantitative temperature measurements in and around the treatment region(s) non-invasively using magnetic resonance imaging (MRI) before and during thermal therapy to monitor and control treatment from a heating applicator.

BACKGROUND

Thermal coagulation therapy may be used for the treatment of localized diseased tissue, e.g., tumors, in a diseased organ or body. Generally, a target volume of tissue is sufficiently heated to achieve a therapeutic effect, such as thermal coagulation. Tissue thermal coagulation depends on a number of factors, and temperatures in the range of 55-60° C. are generally considered sufficient to provide enough energy to cause such coagulation. Cell death results from heating to these temperatures, and a region of irreversible thermal damage can be observed with imaging following the treatment. In addition, heating can be produced from minimally-invasive applicators, eliminating the need for open surgery, and potentially reducing recovery time and morbidity for patients. This approach has been used with some success in the treatment of isolated primary liver cancers and colorectal metastases for patients otherwise ineligible for surgery.

Interstitial thermal therapy is currently practiced by inserting heating applicators directly into a target site within an organ. Several energy sources have been integrated into interstitial heating applicators, including lasers, ultrasound, microwave, and radiofrequency energy. Preferably, interstitial thermal therapy delivers sufficient thermal energy to coagulate an entire target volume, while avoiding undesirable thermal damage to normal tissue. This strategy is referred to as "conformal thermal therapy." One limitation of present interstitial thermal therapy technology is the inability to control or adjust the three-dimensional pattern of energy deposition dynamically during a treatment. Most current applicators act as point or line sources of energy resulting in highly symmetric patterns of energy deposition in tissue. This makes it difficult to treat targets with complex geometry accurately, and does not take full advantage of the imaging information available with imaging technology such as magnetic resonance imaging (MRI).

One application of interstitial heating is transurethral prostate thermal therapy, which selectively destroys diseased prostate tissue using a device located within the prostatic urethra, and preserves adjacent normal tissues such as the rectal and bladder walls. Disease targets include prostate cancer and benign prostatic hyperplasia (BPH). Current transurethral thermal therapy technologies are incapable of producing a thermal treatment (cell death) pattern that conforms accurately to the geometry of the prostate gland or to selected regions of the prostate gland or other organ or tissue undergoing treatment.

In conformal prostate thermal therapy applications, it is often desirable to implement some form of quantitative temperature monitoring for feedback during treatment to ensure accurate delivery of energy to the prostate gland. Temperature monitoring of treated (or heated) tissue regions can be accomplished in several ways. These include direct measurements as well as indirect measurements of the spatial and/or temporal thermal field in the treatment region.

Magnetic resonance imaging ("MRI") has been used to non-invasively measure spatial heating patterns in tissue. Several MRI techniques are available to measure the temperature distribution in tissue. These techniques are possible because of the temperature dependence of various nuclear magnetic resonance ("NMR") biophysical parameters such as T1, T2, diffusion, magnetization, and proton resonant frequency. The most commonly used technique in MRI-guided thermal therapy is the proton resonant frequency ("PRF") shift technique, which exploits the direct proportionality between the resonant frequency of water protons and temperature. A common technique to measure this effect employs the subtraction of a baseline phase image obtained prior to heating from a phase image obtained during heating to measure the change in phase resulting from local temperature elevations. The change in phase can then be related to the change in temperature through the expression, $$\Delta T(x, y) = \frac{\Delta \Phi_t}{\alpha \cdot \gamma \cdot B_o \cdot TE}$$

where $\Delta T$ is the temperature change between two images, $\Delta \Phi$ is the phase change between the same two images, $\alpha$ is the proton resonant frequency shift coefficient (typically −0.01 ppm/° C.), $\gamma$ is the gyromagnetic ratio, $B_o$ is the strength of the main magnetic field (T), and TE is the echo time of the imaging sequence used to acquire the two images.

A phase subtraction technique is required due to large static background phase variations in MR images due to inhomogeneities in the main magnetic field, which are much larger than the phase changes due to temperature. Unfortunately, MR thermometry using the phase subtraction technique is limited in its accuracy by a number of issues including drift in the main magnetic field, inter-image motion, susceptibility-induced temperature artifacts, inaccurate baseline estimates, and relative motion of the detector and the measured subject.

SUMMARY

The present invention includes a thermal therapy method using an ultrasound heating applicator to generate site-specific thermal lesions in diseased tissues which conform to a target volume and boundaries established by medical imaging, e.g., magnetic resonance imaging (MRI). Various embodiments of the invention can be used within an MR imager, permitting non-invasive real-time temperature measurement of the treatment volume and visualization of regions of thermal damage.

According to one or more aspects of the invention, tissue temperature measurements obtained with MRI during tissue heating provide feedback for generating site-specific thermal lesions that conform to the boundaries of the target diseased tissue volume while minimizing thermal damage to adjacent normal tissues. Control over the temporal and/or spatial pattern of energy deposition comes from the directional nature of the ultrasound beam produced by a multi-element heating applicator, wherein the depth of heating from each element can be controlled by adjusting its output ultrasound power and frequency.

In one or more embodiments of the invention, ultrasound energy is used to generate thermal lesions that conform to the target volume, e.g., a 3-D volume, of an abnormal prostate gland for the treatment of prostate diseases, including but not limited to prostate cancer and benign prostatic hyperplasia (BPH).

In one or more embodiments of the invention, temperature measurements made with MRI at or near the boundary of the target tissue volume control the output of the heating applicator or elements thereof. The applicator elements can take the form of transducer elements, individually assembled or made by segmenting a single original transducer element. In one or more embodiments of the invention, the measured boundary temperature is used to control any or all of: the scan rate, power, and frequency of each element of the heating applicator such that the entire target volume boundary reaches a target therapeutic temperature. In addition to absolute temperature metrics, other thermal metrics may be used to design, measure, and determine the appropriate treatment. For example a thermal dose, flux, or elevation above a fixed or variable thermal threshold can be used. The magnitude and frequency of the electrical signal delivered to each applicator element can be manipulated simultaneously providing control over the 3-dimensional shape of the thermal lesion created in tissue.

In some embodiments of the present invention, an ultrasound applicator includes one or more transducers provided with acoustic matching layers to enable operation at multiple frequencies for optimal control of the depth of thermal coagulation. In one or more exemplary embodiments, a plurality of frequencies may be delivered simultaneously from the same transducer, or different frequencies may be delivered from different elements of a transducer.

Additionally, in some embodiments, one or more transducer elements can be controlled independently to generate beams of varying radial depth as a function of the axial position along the applicator, and the entire device can be rotated to control the angular distribution of energy about the applicator's longitudinal axis. According to the invention, the control of all three variables (rotation, power, frequency) during treatment results in the flexibility to control the spatial deposition of energy, and ultimately the pattern of thermal damage in tissue.

In one or more embodiments, a temperature control system is also available wherein coolant is provided to the heating applicator, which can be used to heat or cool the immediately adjacent tissue, as well as remove heat from the transducers. For example, water or another fluid is passed over or near the surface of the transducers. The water or other fluid's temperature may be controlled at its source, and can be used as another factor in controlling the overall treatment process.

According to some aspects, the present invention provides an ultrasound-based thermal therapy method which can reliably produce site-specific thermal lesions in abnormal tissues based on thermal imaging of the tissues. The imaging can be MRI, and the thermal volumes can be controlled in a 3-D volume about an interstitial applicator.

According to some aspects, an MR thermometry-based algorithm is used to effectively control the rotation, power, and frequency of the heating applicator, or elements thereof, in order to achieve a thermal lesion that substantially conforms to the target volume defined by MRI.

Other aspects of the present invention include an ultrasound thermal therapy method which provides thermal ablation of diseased tissues with minimal or no incidental damage to normal tissues near the targeted treatment volume.

Some aspects of the invention provide an ultrasound-based method for site-specific thermal ablation of abnormal prostate tissues.

Aspects of the invention provide an ultrasound thermal ablation method for site-specific treatment of tumors and other abnormalities of the brain, spinal cord, and other organs and anatomical parts of the body.

Further, aspects of the invention are related to the application of MR thermometry to prostate (and other) tissue to provide accurate measurement of the temperature distribution in the prostate gland (and other) tissue during thermal therapy. Aspects of the invention are generally directed to the compensation for errors in the baseline temperature estimate and errors related to susceptibility artifacts, and the correction for such errors in conformal thermal therapy of the prostate and similar organs. Methods of the invention can enhance the accuracy of quantitative temperature measurements during thermal therapy, and provide greater capability to evaluate the errors associated with various approaches.

In general, in one aspect, the invention provides a method for monitoring a thermal effect of a conformal thermal treatment to diseased tissue in a target volume. The method includes acquiring a reference image of the volume containing the diseased tissue at a first position of a device inserted at least partially into the volume, determining a baseline temperature distribution of the reference image, acquiring an image of the volume containing the diseased tissue at the first position and while substantially simultaneously delivering a treatment to the volume, performing a phase subtraction between the image and the reference image to determine a change in phase between the image and the reference image, and determining a current spatial temperature distribution in the volume containing the diseased tissue.

In general, in another aspect, the invention provides a system for monitoring a thermal effect of a conformal thermal treatment to diseased tissue in a treatment volume. The system includes an imaging apparatus configured to acquire a reference image of the treatment volume for a first position of a thermal applicator positioned to distribute a treatment to the treatment volume, and to acquire a current image of the treatment volume for the first position of the thermal applicator substantially simultaneously with the distribution of the treatment to the treatment volume, and a temperature module configured to determine a baseline temperature distribution for the reference image and perform a phase subtraction between the current image and the reference image to determine a change in phase between the current image and the reference image. The system is configured to determine a current spatial temperature distribution in the volume containing the diseased tissue.

A method to which one or more embodiments are directed includes quantitative monitoring of an effect of a thermal treatment of tissue in a target volume to be treated, by acquiring at least one reference image of the target volume for at least one respective position of a thermal treatment device at least partially inserted into a patient's body such that the thermal treatment device is substantially within or proximal to the target volume being treated, determining a first temperature distribution corresponding to the at least one reference image, acquiring at least one additional image of the target volume, corresponding to the at least one respective reference image, with the treatment device substantially at the respective at least one position, while substantially simultaneously delivering a thermal treatment from the thermal treatment device to the target volume, performing a phase subtraction between the at least one additional image and the respective at least one reference image to determine a change in phase between the at least one additional image and the at least one reference image; and determining a second spatial temperature distribution in the target volume as a result of said delivery of said thermal treatment.

This disclosure also describes methods necessary to overcome the sources of error in prostate MR thermometry during thermal therapy. Those skilled in the art will appreciate that the present concepts can be applied to performing thermal therapy in many other locations within the body. The methods and apparatus provided herein can be used generally on any suitable patient or organ, regardless of gender, and even on human or animal subjects.

Other features and advantages of the present invention will become apparent from the following detailed description. It should be understood, however, that the detailed description and the specific examples, while indicating preferred embodiments of the invention, are given by way of illustration only. Various changes and modifications within the spirit and scope of the invention will become apparent to those skilled in the art from this detailed description.

DETAILED DESCRIPTION

Various embodiments of the present invention are directed to ultrasound heating applicators used to generate site-specific thermal lesions in diseased tissues, conforming to a predetermined three-dimensional (3-D) target volume and boundaries established by medical imaging. One imaging modality that may be used herewith is magnetic resonance imaging (MRI). Temperature measurements made with MRI techniques at or near the boundary of the target volume and/or the maximum temperature within the treatment volume are used to control the scan rate, power, and frequency of the heating applicator and/or of each element of the applicator, such that substantially the entire target volume reaches a predetermined therapeutic temperature or other thermal threshold. In one or more embodiments, the magnitude and frequency of the electrical power signal delivered to each element, and the rotation rate of the entire applicator can be controlled simultaneously, providing a 3-D profile of the thermal lesion created in the diseased tissue. In one or more embodiments, the method of the invention is used to generate a thermal lesion that substantially conforms to the shape of the prostate gland.

Magnetic resonance imaging (MRI) may be used to control the thermal therapy by providing 3-D real-time quantitative thermal imaging information during the treatment. In addition to the temperature distribution measurements, the MRI can be used to visualize the outer margin of cell death due to thermal damage at the time of treatment or shortly thereafter. These features provide "on-line dosimetry" and rapid evaluation of therapeutic outcome during a treatment.

Various embodiments further describe an application of MR thermometry to prostate tissue to provide measurement of the temperature distribution in the prostate gland tissue during thermal therapy. Embodiments of the invention are configured to compensate for errors in the baseline prostate temperature estimate and errors related to susceptibility artifacts. Embodiments of the invention are directed to methods of performing non-invasive thermometry, preferably with MRI, which can be applied for example in the context of thermal therapy treatment. Methods of the invention can enhance the accuracy of quantitative temperature measurements during thermal therapy, and provide greater capability to evaluate the errors associated with various approaches. Treatment of tissues or organs other than the prostate is possible and envisioned.

Figure 1:
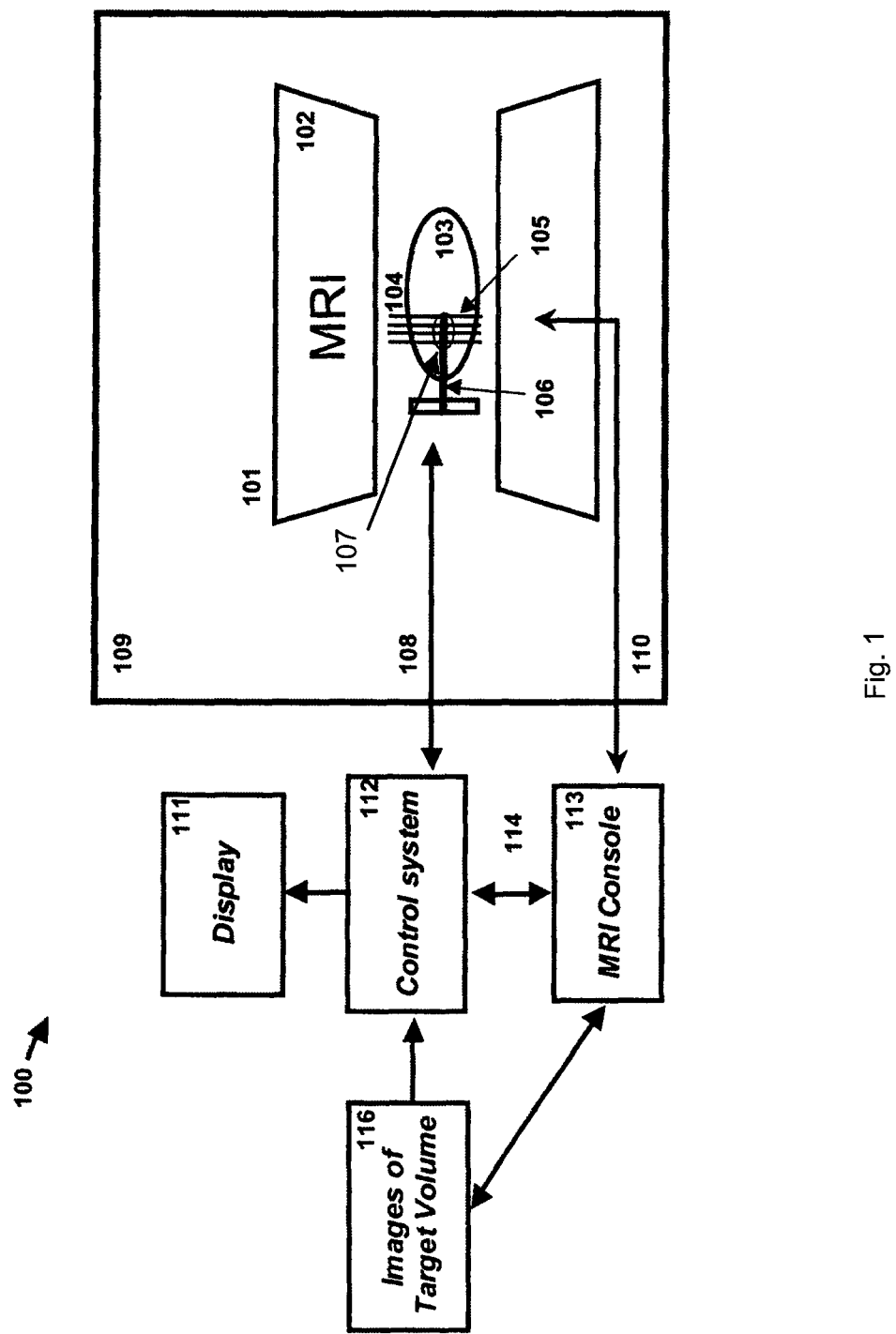
FIG. 1 is a schematic illustrating the basic components used to practice MR image-guided ultrasound thermal therapy according to the present invention.

FIG. 1 illustrates the main components of an exemplary thermal therapy and imaging system 100 according to one or more embodiments of the present invention. An imaging system 101, employing an MRI device 102, is used to acquire a 3-D image data set 116 prior to administration of thermal therapy in order to locate and define a tumor volume and the surrounding anatomy of interest. A target treatment volume 105, which can be the same or similar to the tumor volume, is then prescribed from image set 116, and can include anatomical and functional information important for treatment planning purposes.

The system includes treatment equipment located inside a MR magnet chamber 109, such as a multi-element ultrasound heating applicator 106, motor assembly 107 for controlling device rotation, and the MR imaging device 102 for monitoring and evaluating the progress of a treatment. The MR imaging device 102 is controlled by and sends MRI data 110 to the MRI console 113, located outside the MR magnet chamber 109.

A treatment control system 112 is used to operate motor assembly 107 and heating applicator 106 by passing electrical control and/or actuator signals to this equipment via cables 108 which pass through filtered panels to eliminate RF contamination of the MR imaging process. Treatment control system 112 includes hardware and/or software, including processors, program instructions, data storage devices, network communication devices, or any auxiliary control and actuation device, support algorithm, or system, as needed to achieve its function. Measurements and signals from applicator and motor equipment 106, 107 are sent back to the treatment control system 112 via any suitable conduit, generally referred to herein as cables 108. Shielded wire, fiber-optic, or out-of-band wireless connections may be used as cables 108.

Image data or information corresponding to the acquired MR images is sent to the treatment control system 112 through a connection 114 coupling the MRI console 113 and the treatment control system 112. Alternatively, the MR imaging system 101 can be controlled by the treatment control system 112 through connection 114 coupling treatment control system 112 and MRI console 113.

In one or more embodiments, treatment control system 112 employs treatment planning software to locate and/or define a target treatment volume 105 based on the acquired image data 116 that are displayed on the MRI console 113 and/or an independent display 111. Image data 116 may include conventional MRI images, or other derivative images, data, or information that are adapted for the present purpose. For example, the image data used by system 100 may include filtered, post-processed, amplified, colorized, interpolated, transformed, mapped, or decimated data in raw or processed form, and in any suitable format.

Imaging data 116 can be used to guide the positioning of applicator 106, including final position location, or to determine an insertion path of the heating applicator 106. Imaging data 116 can also be used to obtain an initial set of scanning and operating parameters used to treat the tissue within target treatment volume 105, while minimizing or avoiding thermal damage to surrounding normal tissue 103.

According to one or more aspects of the invention, heating applicator 106 can be positioned within or adjacent to the target volume of tissue 105. In some embodiments, heating applicator 106 is positioned within the urethra in order to perform thermal therapy of the prostate gland. In one or more embodiments, the positioning of heating applicator 106 is facilitated with rapid imaging, e.g., MRI, ultrasound (US), or computerized tomography (CT), to ensure the proper location of heating applicator 106 in relation to the target tissue volume 105. In one or more embodiments, image-guided prostate treatment is performed with MRI using a transurethral applicator.

Once the heating applicator 106 has been inserted into the desired location in the target tissue volume 105, ultrasound energy is delivered to tissue volume 105 to generate a localized spatial heating pattern while tissue temperature measurements are acquired to determine and control the spatial heating pattern. The spatial heating pattern may be controlled as a function of time to result in a spatio-temporally controlled thermal therapy regime applied to the target tissue volume 105.

In one or more embodiments, the spatial heating pattern is determined with MR thermometry methods in multiple 2-D planes 104, but a number of other thermographic techniques could be employed as well including ultrasound imaging, point sensor measurements, or infrared thermography. Furthermore, given sufficient initial condition information, a thermal therapy plan could be designed and executed even in the absence of real-time imaging feedback. Such a treatment could rely on pre-computed treatment parameters generated on a suitable computer, e.g. treatment control system 112 or an off-line computer coupled to the system 100.

The MR image data 116, temperature maps corresponding to 2-D planes 104, and relevant system parameters are displayed on the MRI console 113, display 111, and provided to treatment control system 112 during treatment. A closed-loop treatment may thus be achieved using the information from the acquired MRI data 110, 116 in a control system to determine or modify existing output parameters to the treatment equipment during the actual therapy.

Generally, heating applicator 106 is positioned by axial insertion of the applicator into an interstitial space within or near the target treatment volume 105. Once inserted, heating applicator 106 is rotated about its axis using motor assembly 107 as desired to sonicate, heat, and treat the target volume 105. The rotation of heating applicator 106 is carried out in a controlled fashion, sometimes referred to as a scan rate. In some or all instances, an entire therapeutic regimen can be accomplished using one heating applicator 106 positioned at one axial target location, and properly rotated in an angular dimension. Such a treatment can be adapted to cover a 3-D volume surrounding the heating applicator 106 and can provide control in the axial, radial, and angular dimensions, as will be described in more detail below.

Initial treatment planning parameters may vary according to the specific application at hand. Some parameters that can be used to design and execute a treatment according to aspects of the present invention include applicator scan rate, output power, and frequency parameters for all elements of the heating applicator, and derived from numerical simulations of the heating process, can be used to deliver a thermal treatment without active feedback in locations where dynamic changes in tissue properties or physiological response are not expected to be significant.

In tissue locations where dynamic changes in tissue absorption, blood perfusion, and other physiological parameters are anticipated, real-time medical imaging feedback through MRI data 110, 116 is provided to the treatment control system 112 to adjust the pre-calculated output parameters required to achieve the desired thermal lesion. In some or all embodiments of the invention, MR imaging data 110, 116 provides high temporal and spatial resolution that can be used for precise guidance and spatio-temporal control of the treatment. In some embodiments, such MR feedback information can be used to control the energy distribution from heating applicator 106, without the need for a pre-determined treatment plan.

Effective imaging feedback may be provided by continuously acquiring MR images to quantitatively monitor the temperature distribution in the vicinity of heating applicator 106, wherein such MR thermometry information is used to control the output parameters of heating applicator 106. This control allows adequate heating of the target boundary without overheating the areas near the transducer surface. For example, heating may be carried out until the temperature along the entire target boundary volume 105 is elevated beyond a threshold temperature, or thermal dose, sufficient to achieve a desired therapeutic outcome. In one or more embodiments, the temperature required for thermal coagulation is chosen as a threshold temperature. Once this thermal threshold is reached, images sensitive to thermal damage, e.g., T2-weighted MR images or contrast-enhanced T1-weighted MR images, are acquired to evaluate the spatial pattern of thermal damage generated in the tissue, and compare the damage pattern to the desired target treatment volume 105. Thus, MR imaging is used to provide independent measurement and/or corroboration of the tissue damage pattern predicted by MR thermometry, wherein tissue heating can be terminated or further heating can be performed as necessary. Real-time adjustments to the thermal therapy and the heating applicator 106 driving parameters could be carried out to optimize or correct the course of a treatment after it is underway. According to one aspect of the invention, if the thermal lesion substantially covers the entire target volume 105, the treatment is considered complete, and the heating applicator 106 is de-energized and/or removed from the patient's body. Optionally, serial MR imaging of the target tissue volume 105 and/or the surrounding tissue 103 is performed following the thermal therapy to evaluate relevant physiological and metabolic parameters in or near the treatment zone.

Other attendant steps and devices may be employed in the process of providing the thermal therapy as described above. For example, an acoustically-transparent catheter can be inserted within or adjacent to the target tissue volume 105. The catheter may be first inserted into the prostate gland via the urethra, and the heating applicator 106 is inserted into the catheter to deliver the thermal therapy. Also, other medical or surgical devices and/or pharmaceutical agents can also be inserted down the catheter into the target volume 105 to perform further diagnosis and treatment. An example of such other medical devices includes a miniature radio-frequency (RF) micro-coil, wherein the RF micro-coil can perform high-resolution MR imaging or spectroscopy of the target tissue volume before and after the delivered therapy to evaluate the outcome of the treatment.

An MR imaging coil may be integrated into the outer housing of the transurethral device, wherein the MR coil provides highly directional imaging with excellent signal to noise in the region of heating by the device. Combined with external or endorectal imaging coils as a phased array or in a parallel-imaging strategy, a large field-of-view with acceptable signal-to-noise ratio and a localized region of extremely high signal-to-noise ratio in the region of heating can be achieved. The wide field-of-view provides visualization of the target volume and surrounding anatomical structures, while the localized region of high signal-to-noise can produce temperature measurements of extremely high fidelity for feedback control of the thermal therapy.

Figure 2:
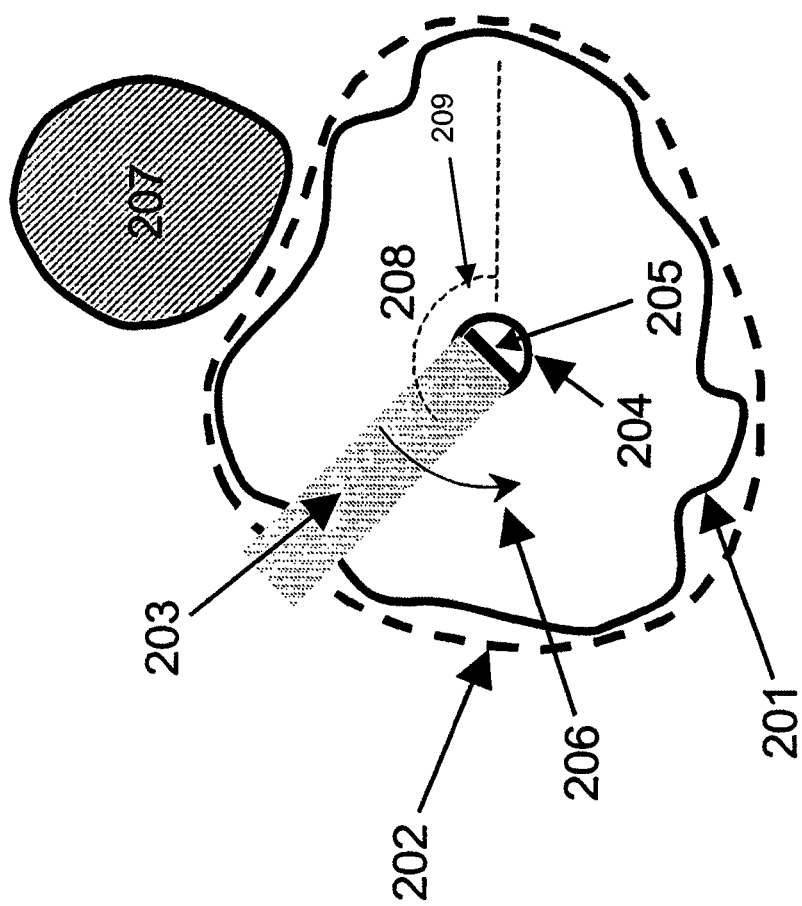
FIG. 2 depicts the concept of conformal thermal therapy from a single directional ultrasound transducer, in the plane of rotation.

FIG. 2 illustrates an example of conformal thermal therapy from a single directional ultrasound transducer, in the plane of rotation. The figure is a planar view with the page being in a plane perpendicular to the axial dimension of a heating applicator 204. In other words, the heating applicator 204 is seen in transverse cross-section with a planar ultrasound transducer 205 integrated into it, which produces a collimated ultrasound beam 203 and resulting heating pattern in the surrounding tissue. The heating applicator can be rotated about its axis to a desired angular position 208, or rotated at a desired angular scan rate 206 during treatment. The angular position 208 and angular scan rate 209 of the heating applicator 204 determine, at least in part, the spatial energy deposition. The target volume 201 can be identified in anatomical/functional imaging information acquired prior to treatment. A treatment volume boundary 202 is chosen so that it substantially encompasses the target volume 201 while generally sparing the surrounding or nearby tissue structures 207. The surrounding or nearby tissue structures 207 may be sensitive or critical structures that cannot or should not be damaged by the thermal therapy. The target volume 201 in this plane is treated by rotating the heating applicator across the entire region. The extent or thickness of this plane of heating is determined by the axial length of a particular element in the heating applicator 204. The degree to which the treatment volume boundary 202 can be controlled to conform to the target volume 201 is related to the rate of heating and the thermal conductivity of the tissue, profusion, and other acoustic and thermal factors.

It should be appreciated that the thermal treatment device can be inserted within a space defined by the diseased organ such as the prostate gland. That is, in some applications hereof, the treatment device is placed substantially within the diseased volume of tissue being treated, and the treatment radiation is delivered from within the volume. In addition, other configurations may be desired whereby the treatment device is placed proximately to the diseased tissue or organ to be treated, and the treatment radiation is applied to the diseased volume from outside the diseased volume.

Figure 3:
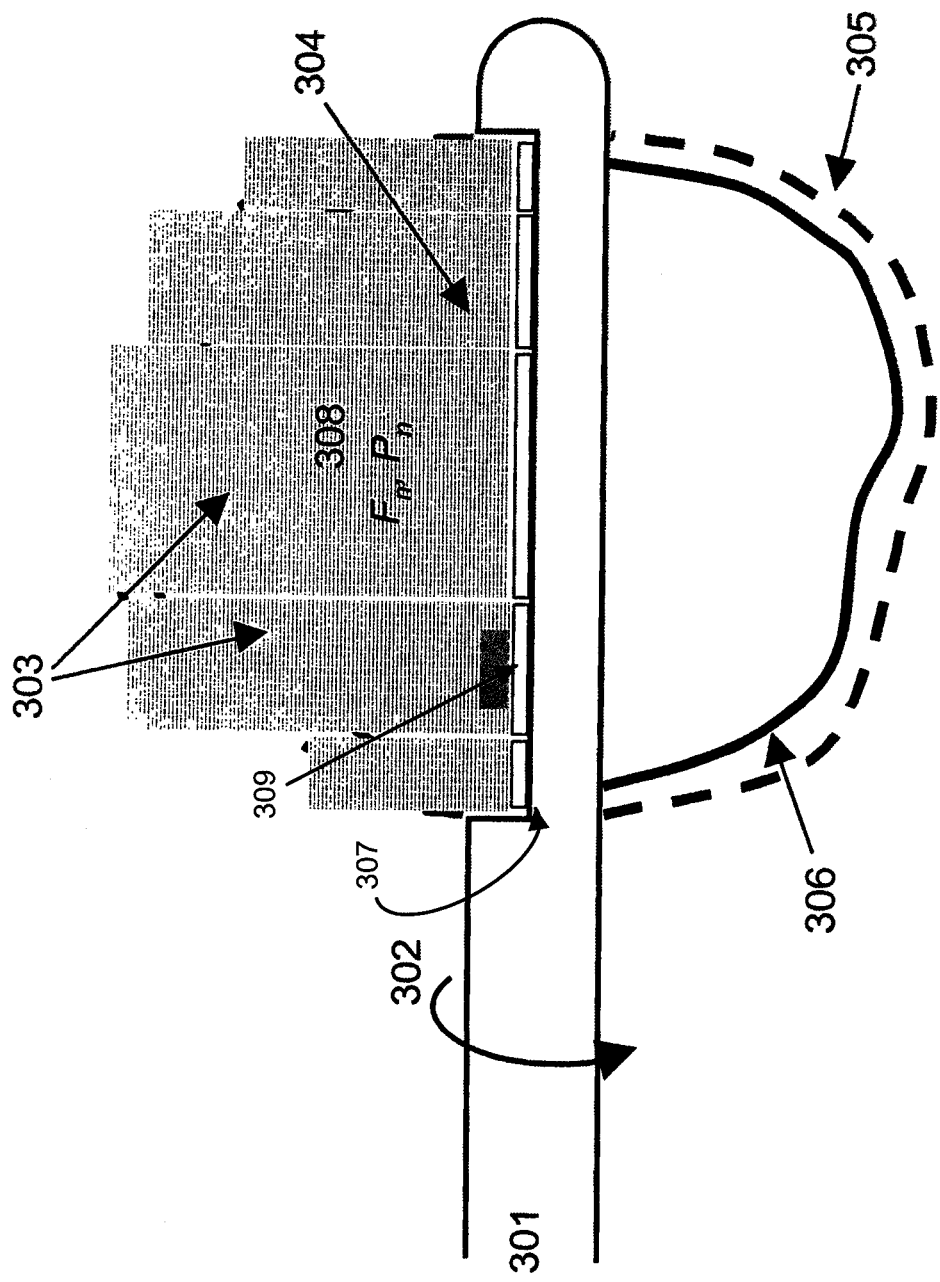
FIG. 3 depicts the nature of conformal thermal therapy using a multi-element ultrasound heating applicator, along the length of the applicator.

FIG. 3 illustrates the nature of conformal thermal therapy using a multi-element ultrasound heating applicator, in a plane parallel to the (axial) length of the heating applicator 301. Corresponding cross-sections of the target volume 306 and the treatment volume boundary 305 are shown in the figure. The heating applicator 301 is inserted into the target volume 306 such that the multi-element transducer 307 is able to treat one angular location of the entire target volume 306 simultaneously. In situations where the target volume 306 is axially larger in extent than the multi-element transducer 307, the heating applicator 301 can be axially translated to cover this increased axial extent. Each element 309 in the multi-element transducer 307 produces a collimated ultrasound beam 303 with a frequency ($f_n$), power ($P_n$) 308 and dimensions determined by the size of the element and other acoustic and design factors. The acoustic energy passes through an acoustic window 304 made from a thin material with a low ultrasound reflection and absorption coefficient. The values of the frequency and power of each element 309 can be adjusted dynamically during treatment based on imaging information acquired during heating. The overall spatial pattern of energy deposition can be adjusted to conform to the geometry of the target volume 306. The rotation 302 of the heating applicator 301 can be seen in the figure, and generally applies to all of the elements 309 in the device if they are coupled through a common structure.

Figure 4:
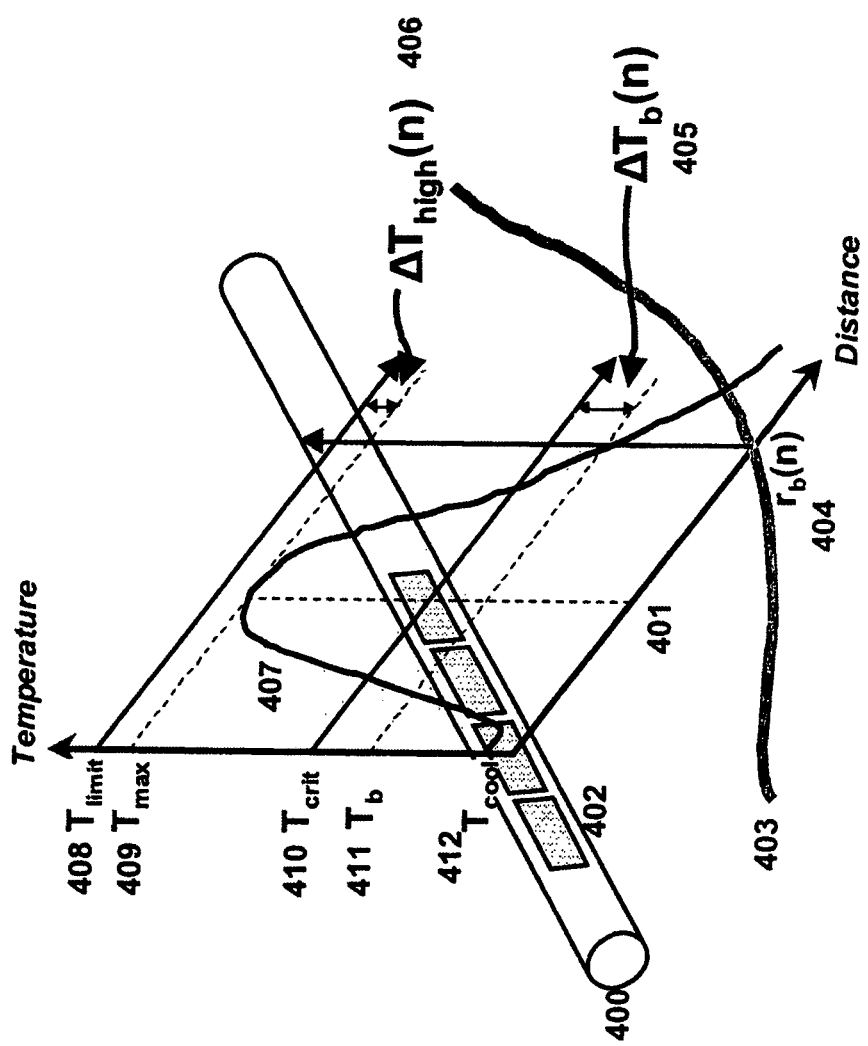
FIG. 4 shows the nature of the temperature distribution produced by an ultrasound transducer in tissue, and the relevant parameters that are used to control heating.

FIG. 4 illustrates the nature of the spatial temperature distribution produced by an ultrasound transducer in tissue, and the relevant parameters that are used to control heating in an exemplary embodiment. The temperature profile 407 from a single element 402 reaches a maximum value $T_{max}$ 409 at some distance 401 from the surface of the heating applicator 400, typically 6-8 mm. The temperature immediately adjacent to the heating applicator is closer to the temperature of the cooling water flowing through the applicator ($T_{cool}$ 412) during treatment. Further away than 401, the temperature profile 407 decreases with distance from the heating applicator 400. The target volume boundary 403 is partially shown being at about a distance $r_b(n)$ 404 for the nth element in the heating applicator. The temperature at this distance is denoted by $T_b(n)$ 411. During treatment, it is desired to elevate the temperature 411 at the target volume boundary 404 to a given thermal threshold, $T_{crit}$ 410. The difference between $T_b(n)$ 411 and $T_{crit}$ 410 is referred to as $\Delta T_b(n)$ 405. It should be understood that a corresponding temperature profile would exist for each of the other elements of the heating applicator 400 so that an overall thermal output along the entire active transducer face and extending into the treatment volume is generated as a result of operating and driving the transducer elements. And it should be further appreciated that rotating heating applicator 400 about its axial axis would sweep out an angular spatially and temporally dynamic treatment zone as described above.

In some or all instances, the treatment plan may keep the maximum temperature along the ultrasound beam, $T_{max}$ 409, below an upper limit $T_{limit}$ 408 where unwanted effects in tissue such as tissue boiling, vaporization or charring may occur. Note that this maximum temperature may be monitored in real-time using MR imaging as described earlier, or using thermometry of any other suitable kind. The difference between $T_{max}(n)$ 409 and $T_{limit}$ 408 is referred to as $\Delta T_{high}(n)$ 406. The values of $\Delta T_b(n)$ 405 and $\Delta T_{high}(n)$ 406 can be measured with MR thermometry in one or more embodiments of the invention. Both $\Delta T_b(n)$ 405 and $\Delta T_{high}(n)$ 406 for each element may be incorporated into a treatment algorithm used to perform conformal thermal therapy.

Figure 5:
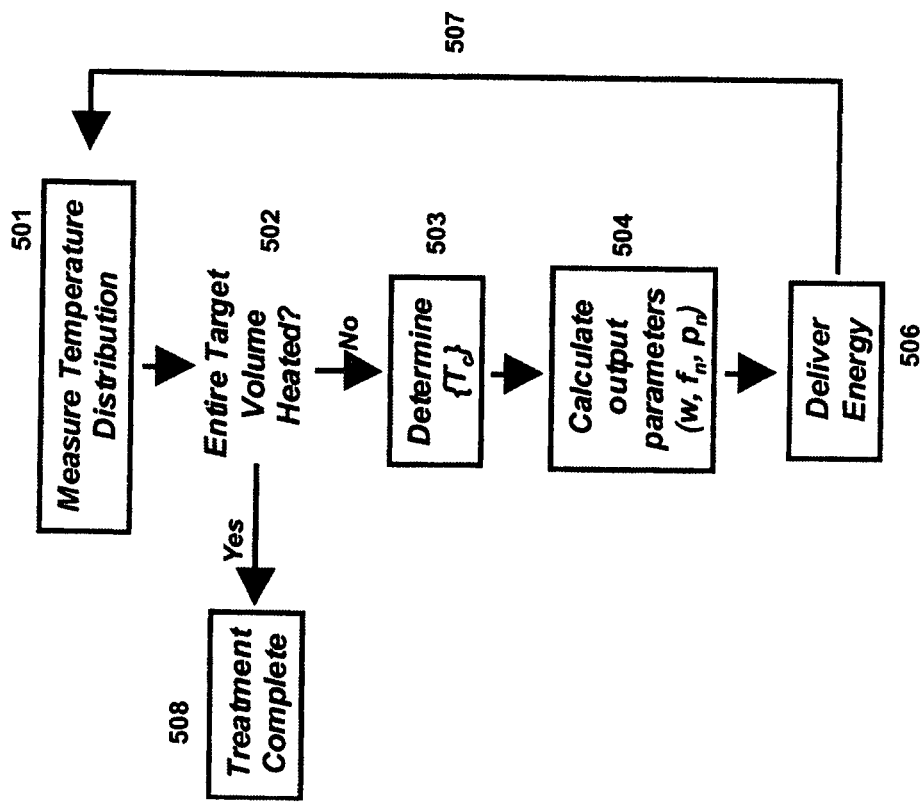
FIG. 5 illustrates the general method for performing MRI-guided thermal therapy with a multi-element ultrasound heating applicator.

FIG. 5 illustrates some steps of an exemplary method for performing image-guided conformal thermal therapy with a multi-element ultrasound heating applicator. The temperature distribution within the target volume is measured at step 501 to evaluate whether the entire target region has reached a desired temperature at step 502. The temperature measurements are made with MRI thermometry, and are either a volumetric or multi-slice acquisition. If the entire volume is heated to the desired level, the treatment is considered to be complete at step 508. If areas remain to be heated, the system determines the temperature at a collection of control points, resulting in a set of input control temperatures $\{T_c\}$ at step 503 used in the control algorithm to determine the output parameters of the heating device at step 504. These input temperatures include, but are not limited to the boundary temperatures for each element, the maximum temperature for each element, and the temperatures along the target boundary in advance and behind the current location of the ultrasound beam (refer to FIG. 4).

In addition, the temperatures along critical anatomical structures can be included in the control algorithm to ensure these structures do not experience undesirable levels of heating. Once the output parameters 504 such as rotation rate of the heating applicator (w), and the power and frequency to each element ($P_n$, $F_n$) have been determined, the values are updated, and the temperature distribution is re-measured at some time later during the delivery of ultrasound energy 506. It should be noted that numerous other steps and acts may be performed in addition to those illustrated. Also, equivalent or substituted acts and steps may be provided in place of those shown as will be appreciated by those skilled in the art and depending on the precise application at hand. For example, a thermal profile/image may be measured prior to beginning the thermal therapy and/or following the completion of the thermal therapy for reference.

Figure 6:
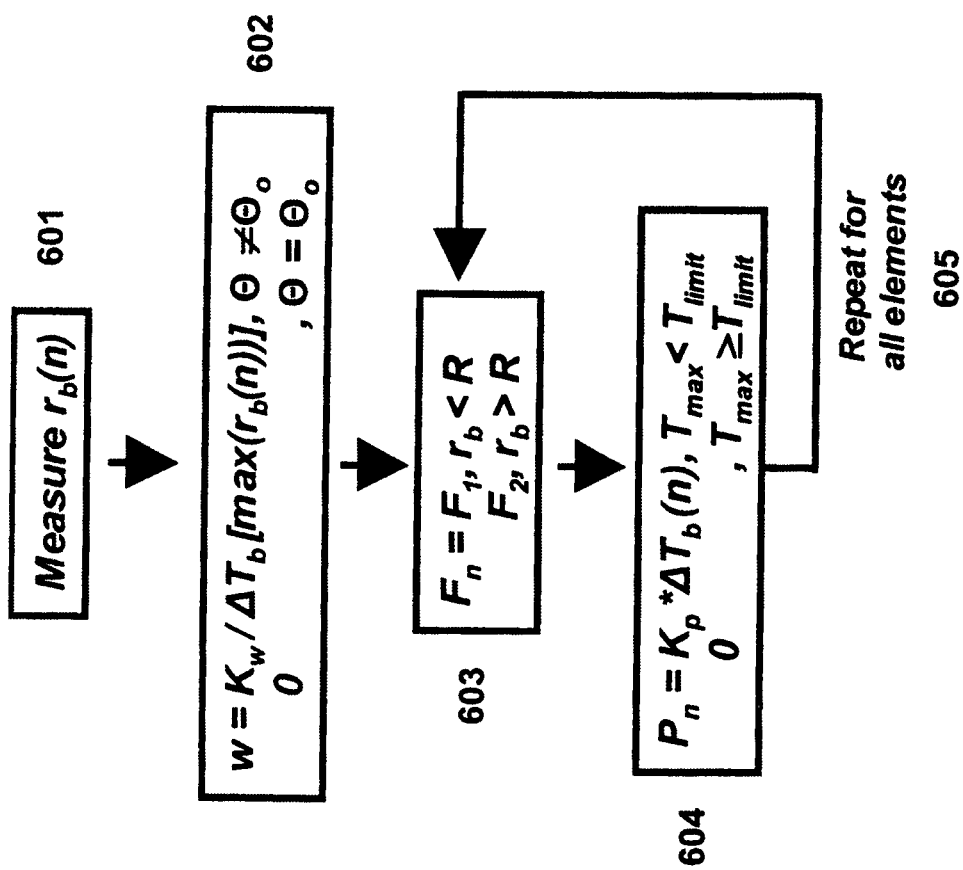
FIG. 6 is a non-limiting example of a control strategy to select an appropriate rotation rate, ultrasound power and frequency based on temperature measurements at the boundary of the target volume and the maximum temperatures within the volume.

FIG. 6 is a non-limiting example of a control algorithm that can be implemented to select an appropriate rotation rate (w), ultrasound power ($P_n$) and frequency ($F_n$) based on temperature measurements at the boundary and within the target volume (step 601). In one or more embodiments, a thermal treatment algorithm produces a heating pattern at an initial angular position (angle) $\Theta_o$, with the device kept stationary at step 602, and the ultrasound power and frequency to each element in the applicator chosen to reach the desired thermal threshold at the target boundary in a relatively short time. The initial frequency is chosen based on the target volume boundary radius of $r_b(n)$ at each element. The temperature at the target boundary for each element is measured and a proportional-difference control relationship is applied to adjust the power such that the boundary reaches a desired temperature.

Upon reaching the desired thermal threshold at angle $\Theta_o$, the applicator is rotated with a scan rate selected that is inversely proportional to $\Delta T_b$ at the target boundary. According to one or more aspects of the invention, the applicator delivers power to each element at a power level that depends on the target boundary temperature at step 604, and at a frequency that depends on the radius of the target boundary at step 603. In the 3-D control algorithm of this invention, the scan rate is selected based on the element with the largest target radius ($\max(r_b(n))$) corresponding to the lowest rotation rate 602. Once the rotation and heating is initiated, the algorithm prospectively evaluates points along the target boundary for any large transitions in radius. If a transition is found close to the current position, the applicator can be rotated quickly to that point in order to minimize heat conduction to tissues peripheral to the target tissue volume. The above process is repeated until the entire target volume has been heated to the desired temperature required for a particular therapeutic effect.

Frequency may be controlled based on the depth of the target boundary. In some embodiments, higher frequencies are used to heat targets at or near the transducers, e.g., at distances less than 14 mm, while lower frequencies are used to heat deeper targets, in order to minimize the time required to heat to the desired depth and to enhance the range of heating available to the heating applicator.

The exact heating radius is generally dependent on tissue type and ultrasound frequency, and can be varied depending on location. In one or more embodiments of the present invention, the treatment control method also assesses the location of the target boundary ahead of the current heating location. This can compensate the treatment parameters to minimize the adverse effects of thermal conduction on the ability to shape the heating pattern sharply. In some embodiments of the invention, a 3-D control algorithm controls some or all of the elements simultaneously to form a coupled system, wherein power and frequency parameters are independently controlled for some or all transducers, but the rotation is fixed for the entire device.

Control of the output of the heating applicator can be accomplished in a number of ways in order to produce a conformal thermal lesion or damage pattern in the prostate gland. Quantitative MR temperature measurements can be used as feedback to control the output of the device until a targeted heating pattern is achieved. MRI can measure the temperature distribution in tissues with good spatial resolution (~1-2 mm), temporal resolution (~5-10 sec) and temperature resolution (~2° C.) in multiple planes during a thermal therapy. Also, quantitative information can be used to assess the spatial heating pattern produced during a treatment.

The heating pattern from heating applicators is generally directional, and depending on the design, can even be highly directional. The temperature distribution along the beam direction is used to provide feedback to the heating applicator and/or the applicator translation-rotation apparatus to control transducer frequency, power and rotation rate. As the heating applicator rotates about its axis, the temperature control point is also moved, so that it is generally oriented along the beam direction, and such that the threshold for thermal coagulation is achieved along the entire target boundary by the end of the treatment. In some embodiments of the invention, a multi-element ultrasonic transducer is used, wherein the control algorithm reduces a 3-D problem to a collection of 1-D control algorithms by considering the temperature profiles along the beams of each element in the transducer.

The control relationships employed in the method of the invention can be determined empirically using a bio-heat transfer simulation of the heating to assess the accuracy and utility of the method to conform heating patterns to the boundary of the prostate. Prostate geometries can be obtained from clinical MR imaging data of patients with confirmed prostate cancer. In an exemplary case, the empirical relationships between the temperature at the target volume boundary and the output parameters of the heating applicator are given by:

$$F = \begin{cases} F_{high}, & r_b < 13.5 \text{ mm} \\ F_{low}, & r_b > 13.5 \text{ mm} \end{cases}$$

$$P = \begin{cases} K_p \cdot \Delta T_b, & T_{max} < T_{limit} \\ 0, & T_{max} > T_{limit} \end{cases}$$

$$w = \frac{K_w}{\Delta T_b}$$

where P is the acoustic power, w is the rotation rate, F is the ultrasound frequency, and $K_p$ and $K_w$ are gain constants associated with the control algorithm. $T_b$ is the difference between the boundary temperature and a target critical temperature necessary for thermal coagulation.

Figure 7:
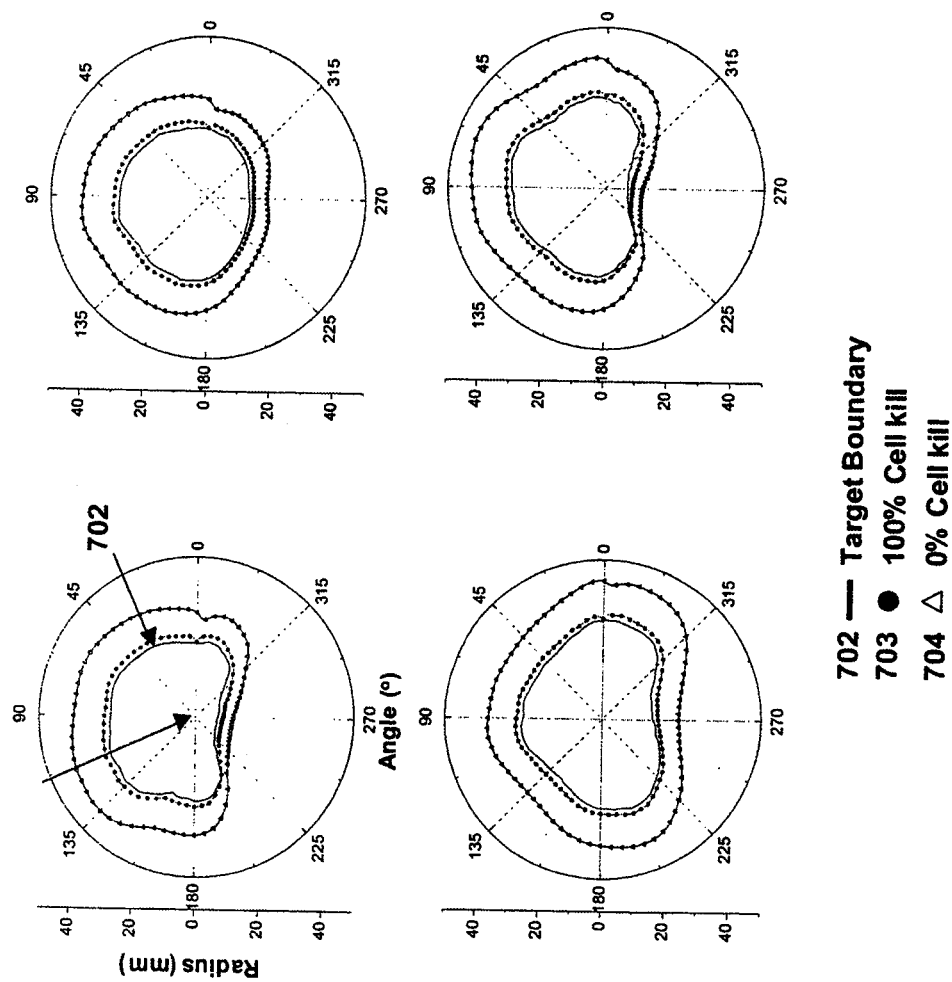
FIG. 7 shows four non-limiting examples from computer simulations demonstrating the capability to perform conformal thermal therapy of the prostate gland using a directional ultrasound heating applicator.

FIG. 7 illustrates four exemplary outcomes using the above-described computer simulations demonstrating the capability to perform conformal thermal therapy of the prostate gland using a directional ultrasound heating applicator. Each panel in the figure shows the target prostate boundary 702 derived from a clinical axial MR image of the prostate gland. The boundary with solid circles 703 denotes the region that reached a thermal threshold of 55° C. during the treatment. This level of heating results in rapid and irreversible cell death through thermal coagulation, and is referred to as 100% cell kill 703 in the figure to indicate that substantially all of the diseased cells within this area would be killed by the thermal treatment. The boundary with the open triangles 704 represents the region that was exposed to at least 30 equivalent minutes at 43° C. of thermal isodose (T43=30 minutes). This is a measure of the combined time/temperature exposure standardized to a common temperature. This conservative level of thermal dose is typically considered to be the minimum thermal dose required to observe histological changes in prostate tissue, and represents the boundary outside which tissue would be unharmed by the heating. The contour is thus labeled as the 0% cell-kill boundary 704 in the figure to signify that substantially none of the cells in this region are killed by the thermal treatment. The results in the four panels indicate that the presently-described techniques can provide a variety of controllable conformal thermal therapies using quantitative temperature feedback and an appropriate control algorithm. These calculations involved controlling a single applicator element. The present methods and systems are also applied through multi-element transducer applicators such that a 3-D treatment volume can be scanned conformally with a pre-determined treatment volume using a pre-determined treatment plan. Such volumes and treatment plans can be modified "on the fly" using real-time thermal imaging as described herein.

Figure 8:
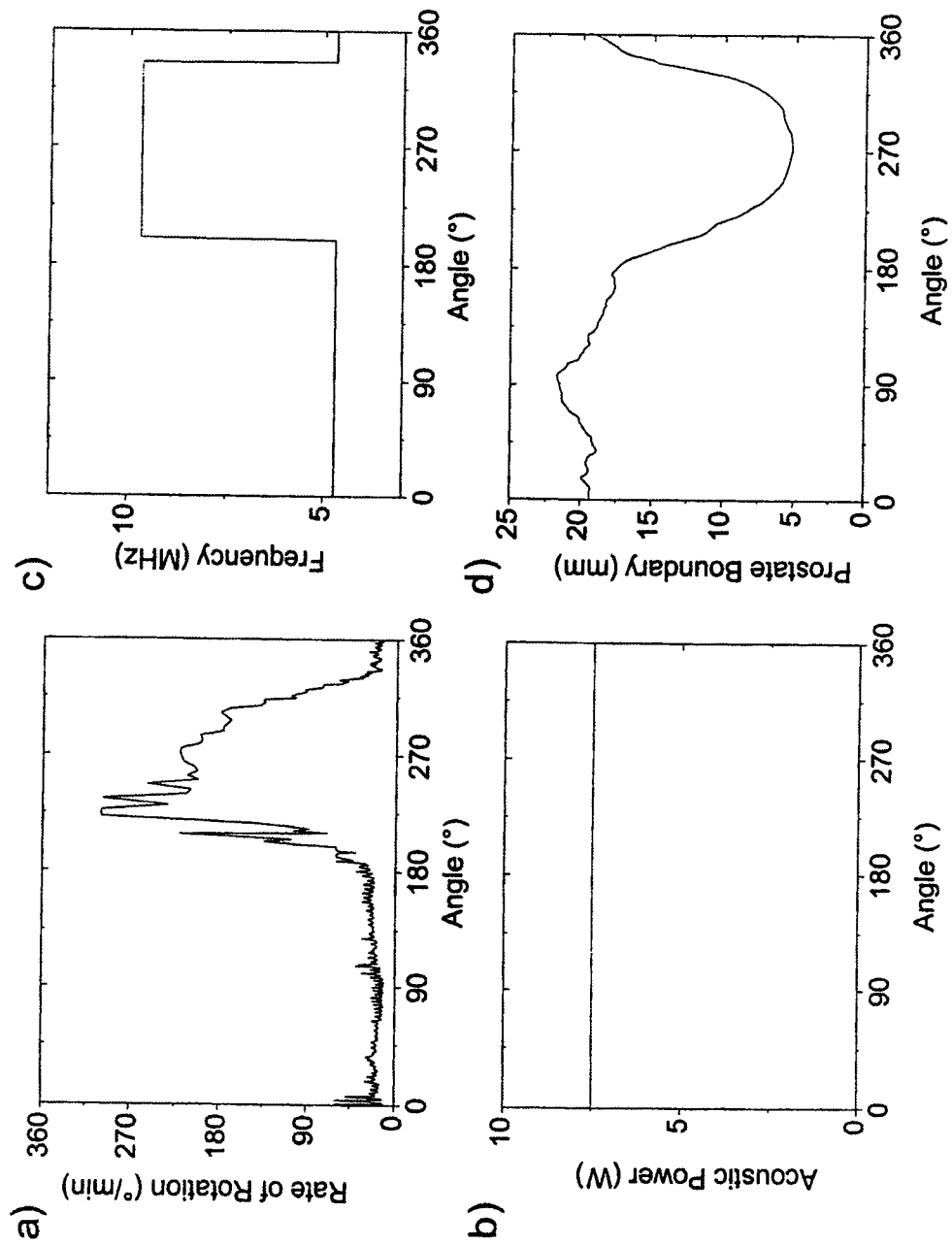
FIG. 8 shows the rotation rate, power and frequency (single element) as a function of angle to treat a target region around a prostate geometry.

FIG. 8 shows an example of the rotation rate, power, and frequency (single element) as a function of angle to treat a target region around a prostate geometry. The effect of rotation rate in this treatment is evident in the top left panel (a). The power (b) was maintained at the maximum allowed level in order to reduce the overall treatment time. The frequency (c) was increased once to improve the conformal heating at the posterior boundary of the prostate gland. The traced prostate boundary is shown as a plot of radius vs. angle in panel (d). In the 3-D implementation of this algorithm, the scan rate is the same for all elements due to the nature of the applicator device.

There are several ways to implement the thermal therapy algorithm of the present invention. In one embodiment of the invention, the treatment is performed without real-time imaging feedback, wherein information about the anatomy and functional status of the target volume is acquired with imaging and other physiological measurement techniques prior to treatment. In this embodiment of the invention, anatomic and physiologic information, including tissue composition, perfusion, and other relevant parameters provide input data to a treatment planning algorithm that models the ultrasound power deposition by the heating applicator and the resulting spatial heating pattern. The temperature feedback control is simulated or determined by measuring the temperature at one or more control points in a simulation, and the temperature measurements are used to control the output parameters of the heating applicator thereby yielding a specific treatment plan for a particular target volume.

In a second embodiment of the method of the invention, a treatment plan based on imaging and physiologic information acquired prior to thermal therapy is delivered to a target region of tissue under imaging guidance. MR thermometry is used to measure the temperature distribution throughout the heated volume during the therapy in order to evaluate the spatial heating pattern, wherein the measured temperatures are used to calculate the expected pattern of thermal damage for comparison with the actual thermal pattern, from which an error function for the treatment can be generated. Upon completion of the therapy, the error function is evaluated and heating re-applied to any regions of the target volume that were insufficiently heated. This process is repeated in order to minimize or reduce the error function.

In yet another embodiment, the heating applicator is positioned within the target volume, and measurements of the temperature distribution are used as inputs for a treatment algorithm to select the output parameters of the heating applicator during the therapy. MRI is used to measure the temperature at a locus of control points which can include, but are not limited to, the boundary of the target volume along the direction of the ultrasound beam, and the maximum temperature in this direction. The temperature measurements are evaluated with the control algorithm to select an appropriate scan rate for the device, and a power and frequency for each transducer element. These applicator device parameters are updated whenever new imaging information is available during the therapy.

Still according to other embodiments of the invention, a treatment plan is devised based on pre-operative imaging and physiologic information, wherein additional imaging information is acquired during treatment and used to update the treatment plan. In some instances, MRI measurements of the temperature distribution of the heated region are obtained during treatment and compared directly against the predictions of the treatment plan, with appropriate adjustments implemented as necessary. Accordingly, this approach takes advantage of the stability of a treatment plan, with an actual physical measurement made with imaging to account for discrepancies between the model and the behavior of the heated tissue. One algorithm of the present invention comprises a 3-D calculation of the heating pattern in tissue, wherein changes in tissue ultrasound attenuation and blood perfusion occurring during treatment are modeled dynamically.

Other aspects of the present invention provide a control system, which takes MR thermometry data from a MR scanner and processes the thermometry data in order to produce instructions for the heating applicator and/or driving apparatus with respect to its output variables. In a particular embodiment, data from the memory of the MR imager is used to calculate and display the temperature distribution from a phased-array coil configuration. The output power and frequency selected by the program, as well as the actual measured transmitted power and scan rate are displayed during treatment. The operator can interact with the system to override the existing output selected by the system, wherein the operator interface can provide the clinical team with predictions of the region of thermal damage, and could monitor important regions of underheating and/or overheating.

Figure 9:
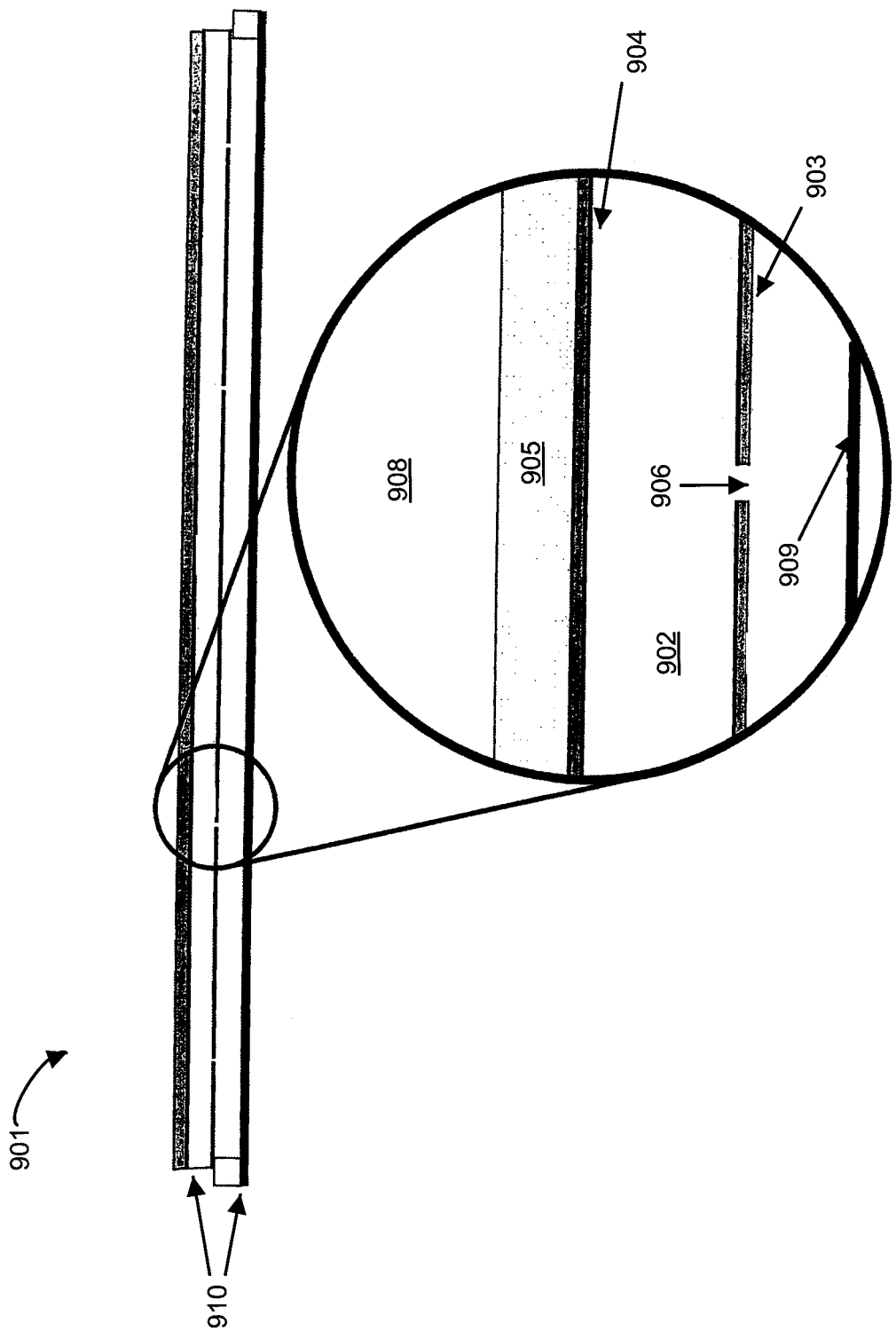
FIG. 9 depicts a multi-element transducer design suitable for integration into the heating applicators of this invention.

FIG. 9 illustrates an exemplary embodiment of a multi-element transducer 901 capable of producing independently-controllable ultrasound radial beams along its length for the generation of arbitrary patterns of thermal damage. The transducer 901 includes a single piece of piezoelectric material 902, preferably a piezoceramic designed for use in high power ultrasonics such as PZT4 or PZT8. A top 904 and bottom 903 electrode are deposited on the surfaces of the transducer to generate an electric field across the transducer. The entire transducer 901 is mounted on a sealed platform 909 with raised edges 910 resulting in a thin backing of air which enables efficient transmission of ultrasound from the front face of the transducer. The thickness of this air pocket is typically at least one acoustic wavelength. In one or more embodiments, the sealed platform and raised edges are made from an insulating ceramic such as alumina. The front surface of the transducer 901 is in contact with water 908 which enables coupling of acoustic energy into the target volume of tissue. If multiple frequency operation is desired, a matching layer of high acoustic impedance 905 can be bonded to the front or back surface of the PZT 902 in order to produce multiple discrete frequencies. In some embodiments, the high acoustic impedance layer is chosen to be one-half the thickness of the PZT 902, resulting in a capability to transmit ultrasound at two discrete frequencies around the original resonant frequency of the transducer without layers.

In some embodiments, multiple independent transducer elements are created by cutting through the back electrode 903 into the ceramic to create multiple, joined elements, wherein the depth of cuts 906 determines the amount of interaction or coupling between adjacent segments. This aspect of the invention provides a practical approach for fabricating a multi-element transducer designed for conformal thermal therapy, wherein multiple elements of varying size can be created.

The performance of the transducer design disclosed in the present invention has been evaluated by obtaining measurements of the impedance spectrum of the elements and the output acoustic power to characterize the stability and efficiency. The effects of the depth of dicing cut 906, the width of dicing cut 906, and the dimensions of the diced elements (width, length) on the output power stability and efficiency have also been investigated. Finite-element calculations have also been conducted to investigate the optimal depth/width of dicing cuts 906.

In one or more embodiments, the individual transducers are connected electrically to a printed circuit board under a platform that houses the transducers, which provides signal paths to a distal point where electrical cables can be connected. This practical design enables adjacent elements to be spaced within 70-100 um of each other (the width of the diced kerf) to minimize under-heated regions of tissue between elements. This approach also provides a simple method for producing arbitrary multi-element configurations capable of producing a three-dimensional pattern of thermal damage conformal to a specific anatomical target. For example, the arrangement and number of elements in the transducer are designed to produce a spatial heating pattern that conforms to the shape of the prostate gland.

Figure 10:
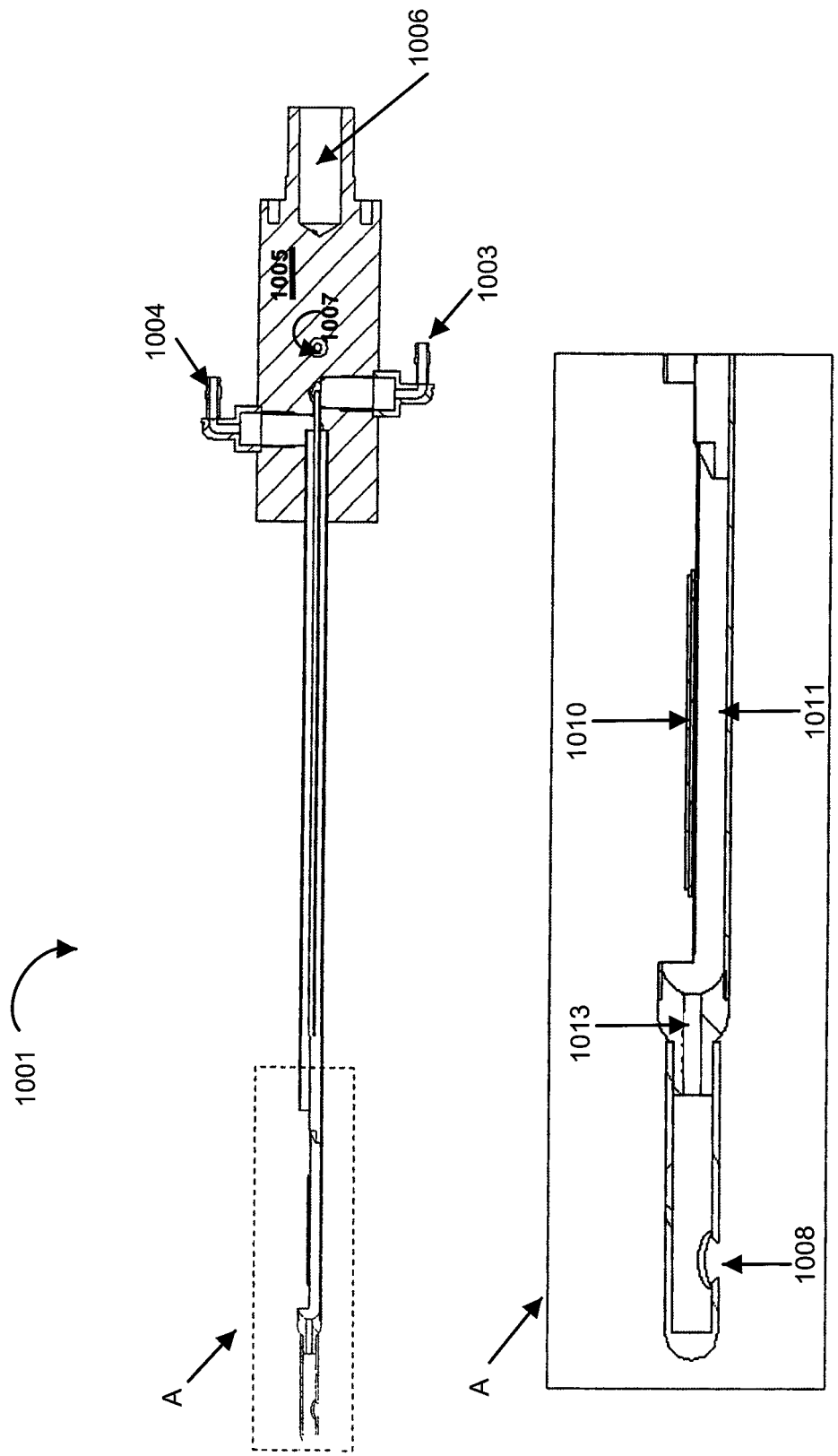
FIG. 10 shows a non-limiting embodiment of a multi-element heating device designed for use in prostate thermal therapy.

FIG. 10 shows a non-limiting example of an ultrasonic heating applicator 1001 designed for transurethral ultrasound thermal therapy. The applicator consists of a multi-element transducer 1010 seated in a rigid tubular housing 1011. This portion of the device is connected to a back end 1005 which includes an inlet 1003 and outlet 1004 port for water or other fluid to flow through the device. The water serves to remove thermal losses from the multi-element transducer 1010 as well as provide acoustic coupling between the transducer and surrounding tissue. The temperature of the water can be controlled in order to heat or cool the adjacent tissue. An additional port 1007 on the back end 1005 can be used to drain urine from the bladder, or flush water through the urethra. The drainage port is connected to an outlet port 1008 located near the tip of the applicator. The tip of the applicator may be flexible, to assist in positioning the device into the prostate gland. A thin tube 1013 connects the outlet port 1008 to the drainage port 1007 in the back end 1005. Electrical signals are transmitted to the multi-element transducer 1010 via low-loss electrical cable which connects to the heating applicator via a multi-pin electrical connector 1006. The heating applicator 1001 can deliver ultrasound energy to a targeted three-dimensional volume in tissue as described in the examples above.

In one or more embodiments of the invention, the heating applicator is a rigid tubular device designed for insertion into the urethra such that the ultrasound emitting portion is located in the prostatic urethra. The device incorporates a substantially planar radiating surface that includes a multi-element transducer 1010. In one or more examples, the dimensions of the individual transducers are between 2 and 4 mm in height (along the diameter of the tubing), and their length is between 5 and 25 mm. The overall length of the multi-element transducer 1010 is designed to substantially cover the entire length of a prostate gland (3-5 cm). However, to treat a gland or organ longer than the transducer, the transducer may be translated along its axial dimension as mentioned earlier.

The frequency of ultrasound produced by these transducers is typically between 4 and 10 MHz, and the resulting ultrasound beam produced by each transducer element can be approximated by a plane wave that is relatively collimated as it passes into the tissue. The number of elements along the active area of the heating applicator is typically five, but the number of elements can be larger or smaller in accordance with the requirement to shape the heating pattern along the length of the device to the contour of the prostate gland or treatment volume.

The heating applicator 1001 may be used in conjunction with medical imaging technology, including but not limited to MRI. Rapid imaging, accomplished with MRI and/or ultrasound can be used to guide the device during insertion to ensure that correct placement is achieved. In one embodiment, during the delivery of ultrasound to tissue, MRI can be used to non-invasively measure the temperature distribution in the region of tissue around the heating applicator to ensure that excessive heating is avoided close to the applicator, and adequate heating occurs at the treatment boundary. For example, upon completion of treatment, MR images sensitive to thermal damage of tissue, such as T2-weighted and/or contrast-enhanced T1-weighted images can be acquired of the treatment volume to assess the extent of thermal coagulation.

In one or more embodiments, the invention includes an ultrasound device for thermal therapy of tissue consisting of a multi-element, multi-frequency transducer, wherein multiple planar ultrasound transducers incorporated in the device produce collimated acoustic fields that heat a localized region of tissue. Rotation of the heating applicator enables the acoustic energy to be delivered to a large volume of tissue, and control over the acoustic power and frequency, as well as the rate of rotation enables the adjustment of the depth to which therapeutic temperatures are achieved. Each transducer can be independently controlled to adjust the heating pattern along the length of the device, resulting in the ability to generate an arbitrary three-dimensional volume of thermal damage.

In some embodiments, the length of the device for transurethral prostate thermal therapy is extended to about 10-12 inches in order to access the prostate gland through the urethra, and the number and size of elements in the multi-element transducer varies specifically with the requirements for achieving conformal heating of the prostate gland. In addition, the device disclosed in the present invention incorporates water cooling through the applicator which serves to remove thermal losses in the transducers, as well as to couple ultrasound energy from the transducers into tissue. Water cooling (or more generally, heat exchange) may be incorporated into the heating applicator to produce convective heat transfer at the acoustic window where the ultrasound beam is emitted. Depending on the flow rate and temperature of the flowing water, this results in local cooling of the first 1-3 mm of tissue adjacent to the device, wherein the urethra and other normal tissues are protected during thermal ablation of anatomically contiguous diseased prostate tissue.

Further improvements in the device of the present invention include an acoustic window cut into the rigid tubing at the location of the multi-element transducer which enables ultrasound energy to pass into tissue. In one embodiment, the window is sealed with a thin polymer layer, which is preferably ~12-25 micrometers thick. In another embodiment, the individual elements are connected with small coaxial cables to a multi-pin connector at the back of the applicator. In yet other embodiments, the 1-2 inch long tip of the device is flexible in order to help navigate the rigid device into the prostate, wherein the tip of this flexible portion is open and connected to a port at the back of the applicator through a thin long tube to allow urine to drain from the bladder during treatment. Yet another embodiment incorporates inflatable balloons at the tip of the device in order to anchor the device by the balloon which is positioned in the bladder.

Figure 11:
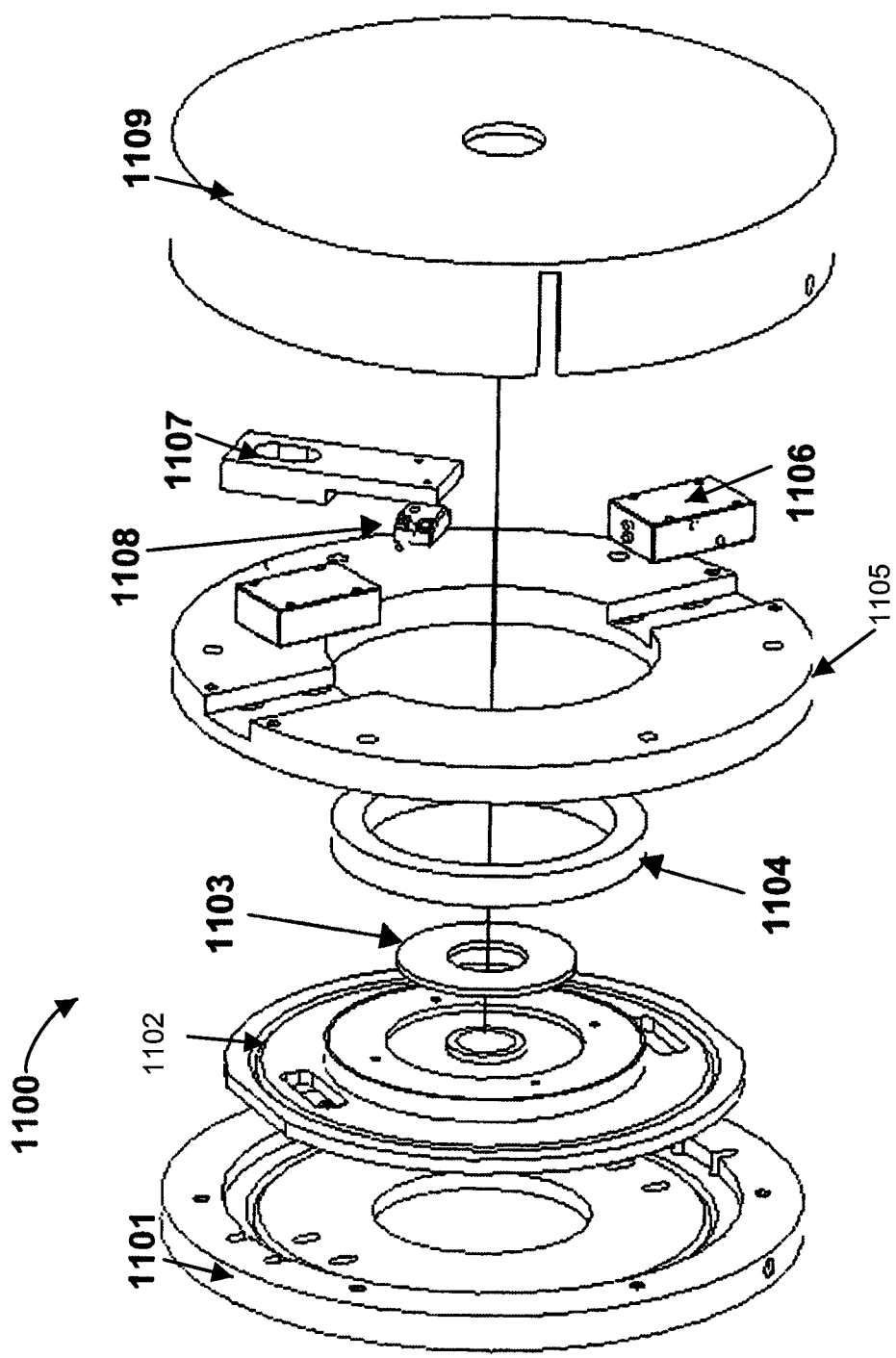
FIG. 11 illustrates a rotation apparatus for angular scanning of a treatment volume.

FIG. 11 shows an embodiment of an MRI-compatible apparatus 1100 capable of rotating a heating applicator to deliver thermal therapy in a clinical MR imager. The apparatus consists of a bearing structure that can be attached to a heating applicator which is driven by MRI-compatible motors. Motor 1106 may be based on a piezoelectric principle, and operate using a sinusoidal driving signal. An encoder including a disk 1103, sensor 1108 and mounting arm 1107 provides positional feedback to a motor controller on the delivery system in order to achieve stable and controlled motion. The bearing structure is made up of a top 1105 and bottom 1101 housing which encase an inner plate 1102 capable of rotation. A ceramic ring 1104 is attached to the inner plate, and is in contact with the piezoceramic motors. A cover 1109 is included to protect the components of the motor from damage. In some embodiments, the assembly is made of MRI-compatible materials including but not limited to plastics, glass, ceramics, and metals such as copper, brass and aluminum.

Figure 12:
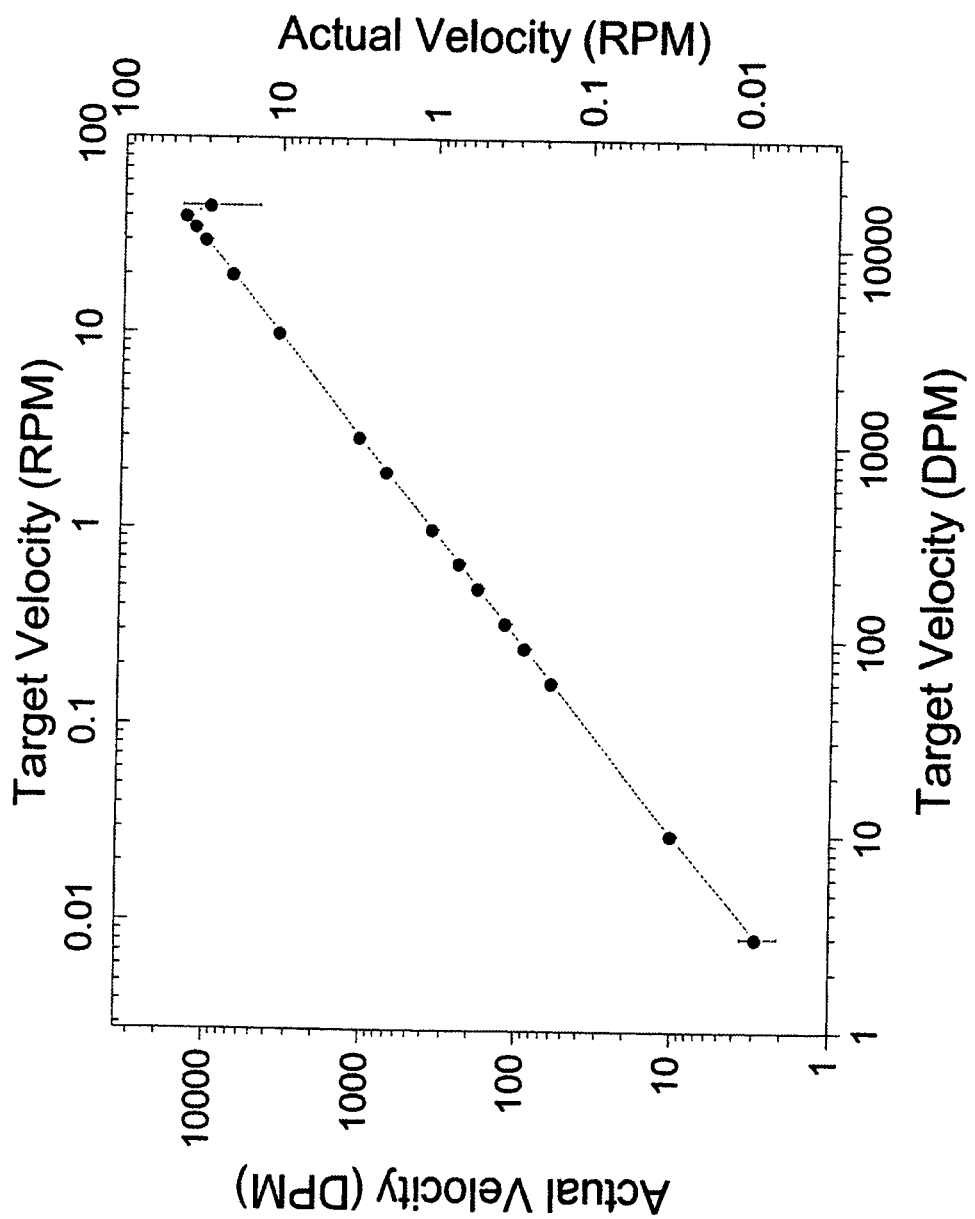
FIG. 12 illustrates the relationship between actual and target velocity of a rotating apparatus for scanning the treatment volume.

FIG. 12 illustrates a non-limiting example of the performance of a prototype MRI-compatible apparatus designed to rotate a multi-element directional heating applicator. The target and actual rotational speeds are shown in two units (°/min, rev/min). A substantially linear relationship exists between the two variables, indicating the system is capable of accurate motion control. The range of motion is large enough to extend over three orders of magnitude, from 0.01 to 30 RPM (3 to 10000°/min). The range of motion is suitable for the required rotation rates to achieve conformal thermal therapy from the multi-element heating applicator described herein, and those skilled in the art will appreciate that many other uses can be realized for such a motion control system in an MRI environment. The described apparatus has been verified to function during the imaging process without producing any measurable interference in the MR images.

Acquiring accurate temperature measurements with MRI in prostate thermal therapy is challenging due to the fact that therapeutic devices or protective cooling devices are inserted into the urethra or rectum in order to deliver energy to the prostate gland while sparing surrounding tissues from thermal damage. Unfortunately, the introduction of devices close to the prostate gland results in both a perturbation of the tissue temperature distribution, particularly if active cooling of the device is implemented, and a perturbation of the static magnetic field if the susceptibility of the device differs from that of tissue. Both perturbations can vary spatially and/or over time. In addition, the prostate can move over the duration of a typical treatment (minutes to hours) for a number of reasons, including respiratory motion, involuntary smooth muscle contraction, rectal peristalsis, and bladder filling/voiding. Finally, motion of therapeutic devices during treatment causes changes in the background magnetic field which affects the baseline image used for subtraction, and can produce temperature artifacts in the prostate gland.

One issue that arises in prostate thermal therapy is motion. Unlike the repetitive motion caused by respiration in organs like the liver, the motion of the prostate is typically smaller, slower, and somewhat random and difficult to predict or model. In addition to respiration, common additional sources of motion include the accumulation of urine in the bladder which results in a translation of the prostate gland, peristalsis of the rectal wall which causes rapid translation (small amplitude) and involuntary muscle contraction, which can result in large static shifts of the prostate gland. Filling of the rectum with gas/fecal matter can also result in a gradual or abrupt translation of the prostate gland. Some of these issues can be addressed through a number of approaches.

Insertion of a draining catheter in the bladder through the urethra can be used to maintain a fixed level of urine accumulation in the bladder, thus reducing the likelihood of prostate translation during treatment. This catheter can be combined with or separate from a catheter used to cool the urethra and surrounding prostate tissue. Alternatively, it can be combined with or be integrated into a device containing the heating applicator for combined drainage and treatment through the urethra.

Peristalsis of the rectum can be a major problem in MRI-guided prostate thermal therapy. One strategy to avoid this is through the use of pharmaceutical agents. Many agents, for example Buscopan™, are known to reduce peristalsis of the gastro-intestinal ("GI") tract, and can be administered prior to or during prostate thermal therapy to reduce rectal peristalsis which causes prostate motion. Reduction of this motion eliminates a large source of error in prostate MR thermometry. Filling of the rectum with gas/stool can be avoided by performing an enema on the subject prior to the therapy to eliminate fecal matter in the lower GI tract. Additionally devices can be inserted into the rectum to block the passage of fecal matter down to the location of the prostate. Devices inserted in the rectum can also be used to cool the surrounding tissue, deliver energy to the prostate for thermal therapy, or both.

Involuntary muscle contraction can similarly be reduced through the use of pharmaceutical agents or by fixation of the prostate gland with devices inserted into the urethra, rectum or both. A combination of devices inserted in both urethra and rectum can serve therapeutic, protective cooling and mechanical fixation purposes simultaneously.

Another source of motion-related artifact is the effect of respiratory motion on external surface coils for MR imaging. The repetitive expansion of the ribcage is the major effect of respiration, but some motion of the anterior surface of the pelvis and lower abdomen can be present. This motion results in the periodic translation of surface coils that may be placed on the anterior pelvic surface during treatment. The effect of this translation is a changing $B_1$ distribution through the prostate, resulting in a different phase distribution in MR images. A method for eliminating or reducing this source of error is to restrain coils on the anterior pelvic surface mechanically so that small motions of the abdomen and pelvis do not alter the coil positions. This is usually not a problem for surface coils located between the patient table and the posterior surface of a supine subject, but coils located within the rectum or urethra should be similarly fixed.

The above combination of urine drainage, administration of muscle relaxants, fixation of coils, and voiding of the GI tract prior to treatment results in the reduction of motion related artifacts which may adversely affect the capability to make quantitative temperature measurements with MRI in the prostate gland during thermal therapy.

Another issue affecting the accuracy of prostate MR thermometry is the assumption of a uniform and constant baseline temperature in the "unheated image" which is acquired prior to energy delivery. In practice, heating applicators and/or protective cooling catheters are inserted into the urethra, rectum, or both prior to treatment for proper positioning within the patient. During the time that elapses from the insertion of the devices to the start of treatment, temperature gradients can build up in the prostate due to thermal conduction between tissue, at about 37° C., and the inserted devices with temperatures usually less than 37° C. For example, the rectum is typically cooled in prostate thermal therapy to protect it from thermal damage, and significant temperature gradients can be generated in adjacent tissues, such as the posterior portion of the prostate if a temperature below 37° C., for example 20° C., is used for the cooling device. Thus an assumption that the initial pre-treatment image is at a uniform and constant temperature can be faulty, resulting in erroneous calculations of the temperature during treatment. In the example of a device cooling the rectum to 20° C., a constant baseline core body temperature assumption would result in overestimation of the temperature achieved in the posterior portion of the prostate gland, and thus undertreatment of this region.

One method to overcome this source of error is a physical approach of first inserting the devices and obtaining the temperature reference image prior to starting the cooling of the devices in the body. This way the initial baseline image is at a constant temperature, provided enough time is allowed for the devices to reach thermal equilibrium with the body. After the acquisition of the initial reference image, the cooling of the devices can be started, and can be observed with MR thermometry. This technique has the advantage of being based on measurement alone, but suffers from the restriction that significant time might pass in reaching thermal equilibrium or between the initial baseline image and the treatment images. The background field may drift over this time or motion might occur. Furthermore, if for any reason a new baseline image must be acquired (e.g. due to motion, or due to a sequential delivery of energy such as in the case of transrectal high-intensity focused ultrasound), one would be left waiting for the temperature distribution to reach equilibrium or substantially reach equilibrium again.

Another approach to correct for this effect is to model or calculate in advance the baseline temperature distribution in the prostate gland due to inserted devices under various appropriate conditions. It can be shown that close to steady state temperature distributions are achieved within a few minutes after device insertion and/or cooling. These distributions can be measured previously under similar conditions or calculated and used to compensate the baseline image. This technique enables acquisition of reference images at any time during treatment, but is dependent on the similarity between the conditions during treatment and the calculations used to determine the baseline temperature distribution.

Another source of error in prostate MR thermometry is related to the static field variations produced by the heating applicator or other inserted devices. Such devices must be made of MRI-compatible materials including plastics, glass, ceramics, and selected metals. However these materials still possess magnetic susceptibilities slightly different from that of tissue, or alternatively a small portion of the device will have a significantly different magnetic susceptibility for functional reasons. An example of this is the piezo-electric transducers ("PZT") used in ultrasound therapy devices, which has a magnetic susceptibility that is significantly different from that of tissue. The result of this susceptibility variation is that the magnetic field around the device is distorted, resulting in greater local variation in background phase pattern. This effect can be compensated by the conventional method of phase subtraction if the device is stationary, apart from the signal loss (and hence increased temperature uncertainty) that can occur in regions of high phase variation. However, if the device moves during the treatment to direct energy (e.g. to different portions of the prostate gland), then the assumption of a static background field is no longer valid and temperature measurements will not be accurate. This error is dependent on the strength of the magnetic field (greater with increasing field strength), the orientation of the device relative to the static magnetic field (less error when device is parallel to Bo), the materials used in the device and their magnetic susceptibility, and the nature of the motion of the device.

One way to correct for the above temperature artifact is to acquire multiple baseline images in all of the possible positions of the heating applicator(s). Then the subtraction during heating can be made from baseline images with the same device positions as those images acquired during treatment. This approach ensures that the field variations caused by the device are the same in the heated and reference images, thus cancelling out this effect. Another approach is to model the field variations produced by the device, and to correct for the device-related temperature artifacts after the subtraction is made. This approach is often difficult due to the number of assumptions made about the geometry of the device, and the magnetic susceptibility of the materials included. If there are only a limited number of positions possible for the device, the multi-baseline approach is a practical approach to implement.

The above effects are numerous and can each introduce errors in the measured temperature distribution during thermal therapy with MRI. A growing number of applications are attempting to use the temperature information acquired with MR thermometry to predict the region of thermal damage, or even to control the amount of heating delivered. This form of "closed-loop" therapy uses the accuracy of the temperature measurements, and errors in the thermometry can result in under-heated regions of targeted tissue, or damage to surrounding structures.

Figure 13:
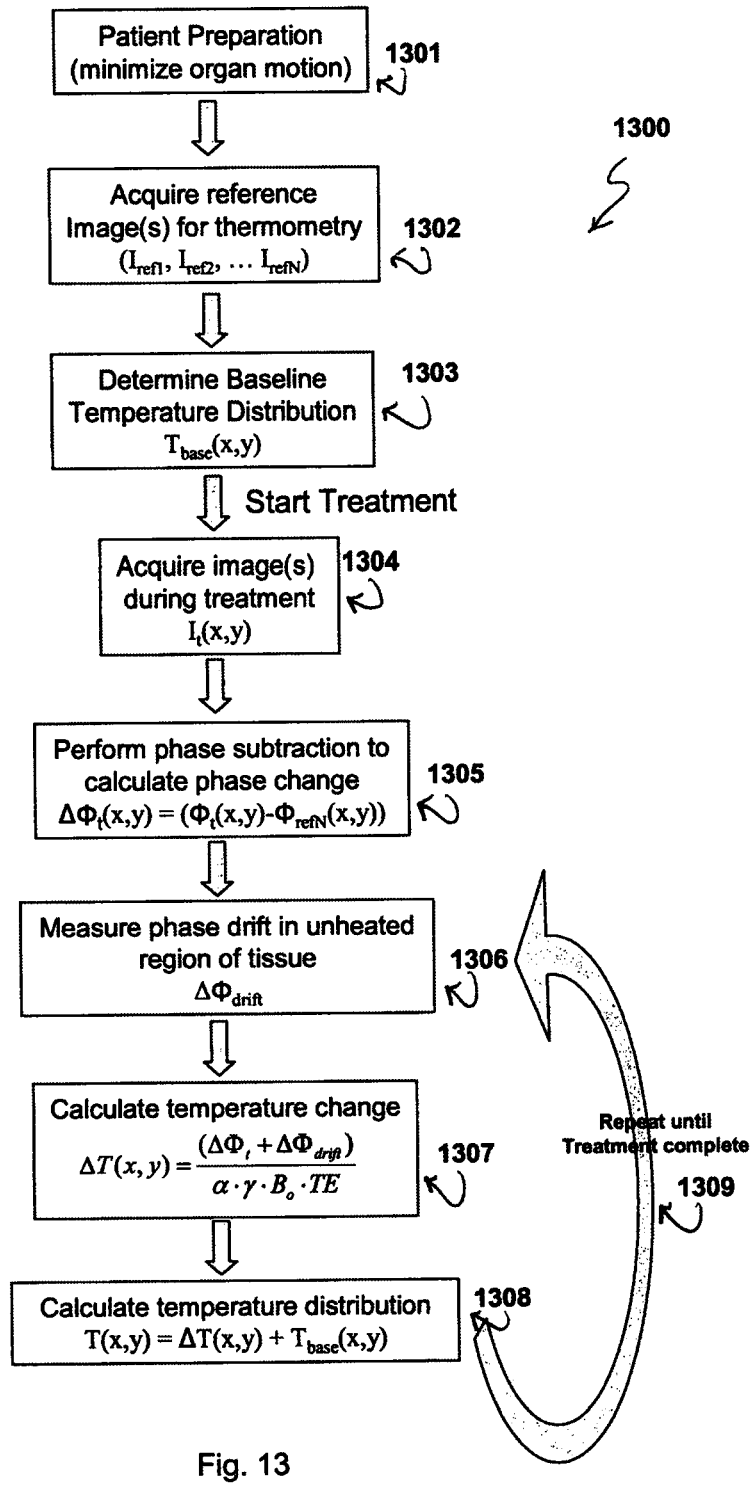
FIG. 13 is a flow chart illustrating a method for obtaining non-invasive temperature measurements during thermal therapy.

Referring to FIG. 13, a process 1300 for obtaining a measurement of the temperature distribution in prostate (or other) tissue during thermal therapy using MR thermometry includes the stages shown. The process 1300 is presented for illustrative purposes only and may include stages in addition to those described.

At stage 1301, the patient is prepared prior to treatment such that the potential for motion of the prostate is minimized. In specific examples, this may include voiding the bladder of urine and maintaining a constant fluid level through the use of a drainage catheter that is separate or integrated with other devices inserted in the urethra. In addition voiding of fecal matter or gas within the rectum and GI tract plus the administration of muscle relaxants targeted to the GI tract can be used to prevent or minimize spurious prostate motion due to rectal peristalsis. The insertion and fixation of heating applicators and cooling devices within the rectum and/or urethra can be used to reduce the possibility of prostate motion, and substantially rigid fixation of surface MR coils on the anterior pelvic surface may also be employed to eliminate or reduce artifacts due to coil motion.

Once the patient is prepped for the treatment, and the appropriate devices are inserted into the rectum and/or urethra, a series of reference images ($I_{ref1}$, $I_{ref2}$, . . . , $I_{refN}$) for thermometry can be acquired, stage 1302. If the devices will remain stationary throughout the treatment, a single reference image might suffice. If there is going to be motion of the device, multiple reference images can be acquired to capture the background phase distribution at each possible position of the device.

At stage 1303, the baseline temperature distribution, $T_{base}$ (x,y) of the reference images is determined. If the entire region (heating devices, prostate and surrounding tissue) is at core body temperature, the baseline temperature is a constant value. If, for example, devices inserted into the urethra and/or rectum are at a temperature different from core body temperature, then a spatially varying baseline temperature must be assigned. The baseline temperature distribution can be approximated by a number of methods, such as through simulations or direct measurement with invasive temperature sensors.

At stage 1304, treatment commences and energy is delivered to the prostate gland from heating applicators. Images are acquired substantially continuously to measure the spatial heating pattern. A phase subtraction is performed for each image acquisition between the current image and the reference image with the device at the same position and orientation to yield the change in phase between acquisitions, $\Delta\Phi_t$ (x,y), stage 1305. The change in phase in a non-heated region of tissue, e.g. adjacent to the treatment volume, can be measured to compensate for drifts in the background phase, $\Delta\Phi_{drift}$ during the treatment, stage 1306. The temperature change between the current image and the reference image is calculated using the well-known proton resonant frequency shift relationship 1307. Once the temperature change, $\Delta T(x,y)$ is calculated, the baseline temperature distribution 1303 is added to determine the current spatial temperature distribution T(x,y) in the heated tissue 1308. The process of image acquisition, subtraction and correction, stages 1306, 1307 and 1308, is repeated as desired, for example, until the end of the treatment.

The method of FIG. 13 is general, and can be applied to other organ systems as mentioned, where the same issues are relevant. In addition, a subset of corrections can be applied in the case where only some of the issues introduced above are present. The method 1300 is valid for thermal therapy involving a single continuous delivery of energy, as practiced in microwave thermal therapy, as well as for treatments that involve sequential delivery of energy to different regions of the prostate, as practiced in transrectal focused ultrasound. In the case of transrectal focused ultrasound the method of FIG. 13 could be applied for each sonication to ensure accurate measurement of the temperature distribution. Additional intermediate corrections and modifications to these steps can be applied. For example, the steps can be performed in an order other than that illustrated in the figure. In addition, the steps can be applied in three dimensions, particularly in the case that multiple imaging planes are being acquired, for example with each step being applied to an individual imaging plane.

Figure 14:
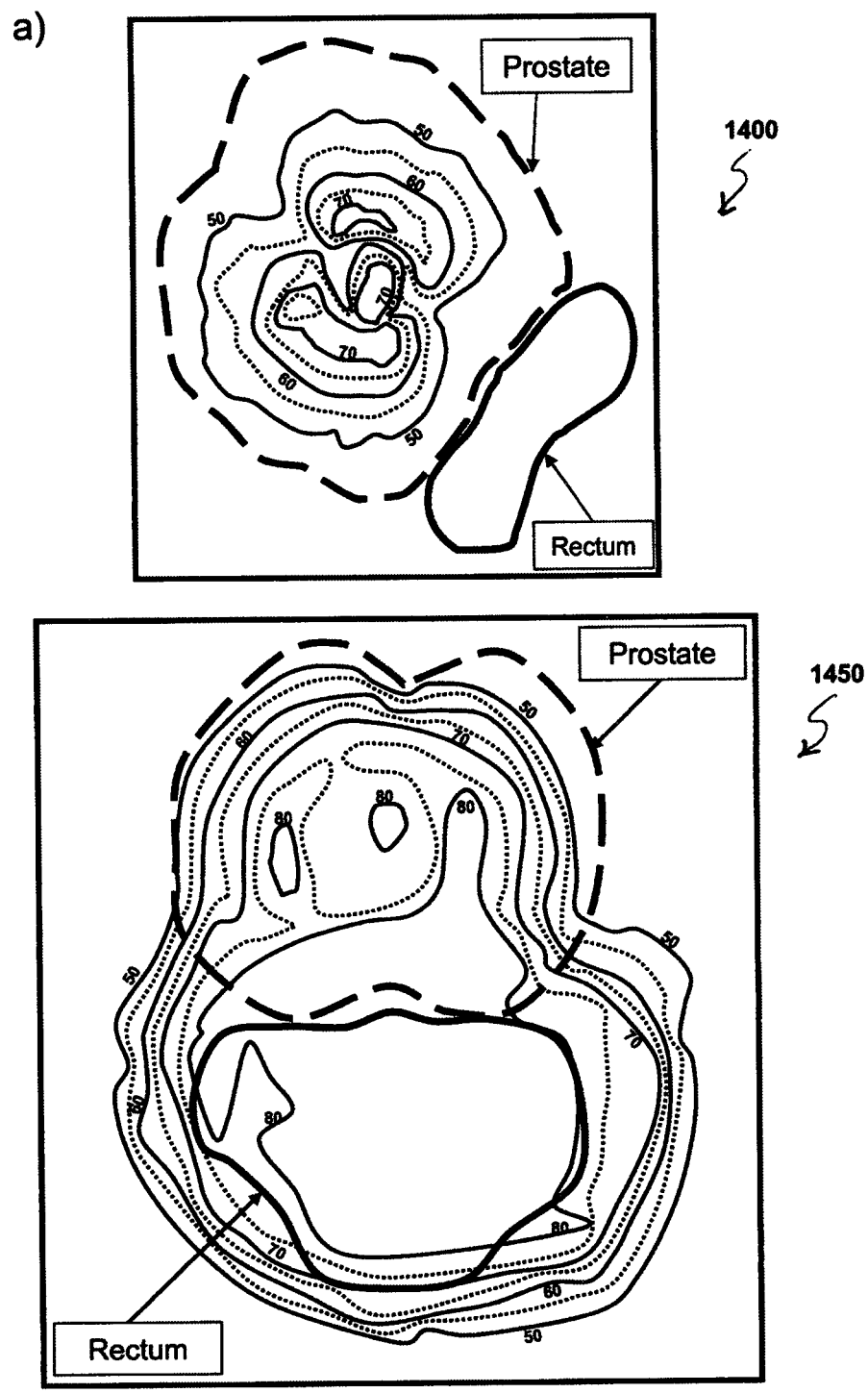
FIG. 14 depicts the impact of rectal peristalsis on the measured temperature distribution in prostate tissue.

Referring also to FIG. 14, a temperature contour map 1400 and a temperature contour map 1450 illustrate instances of a transurethral ultrasound heating applicator used in accordance with the method of FIG. 13. Referring to FIG. 14(a), the cumulative temperature distribution for a dual-sector treatment of a prostate gland in vivo is depicted. The heating can be seen to be continuous and confined to the prostate gland, which is delineated by the heavy dashed curve. Subsequent histology confirmed the accuracy of these temperature measurements. However, as depicted in FIG. 14(b), the cumulative temperature distribution from a treatment where there was motion due to rectal peristalsis is less effective. The motion of the rectum, delineated by the heavy solid curve, produces false temperature changes in the MR thermometry process, and these changes extend into the prostate gland, and disrupt the capability to monitor the spatial heating pattern during treatment. There was significant discrepancy between the measured temperature distribution and subsequent histology in this experiment. Thus, FIG. 14(b) is an exemplary representation of a circumstance that is unacceptable for use as temperature feedback in a 'closed-loop' treatment of patients or to accurately confirm the extent of the heated region.

Figure 15:
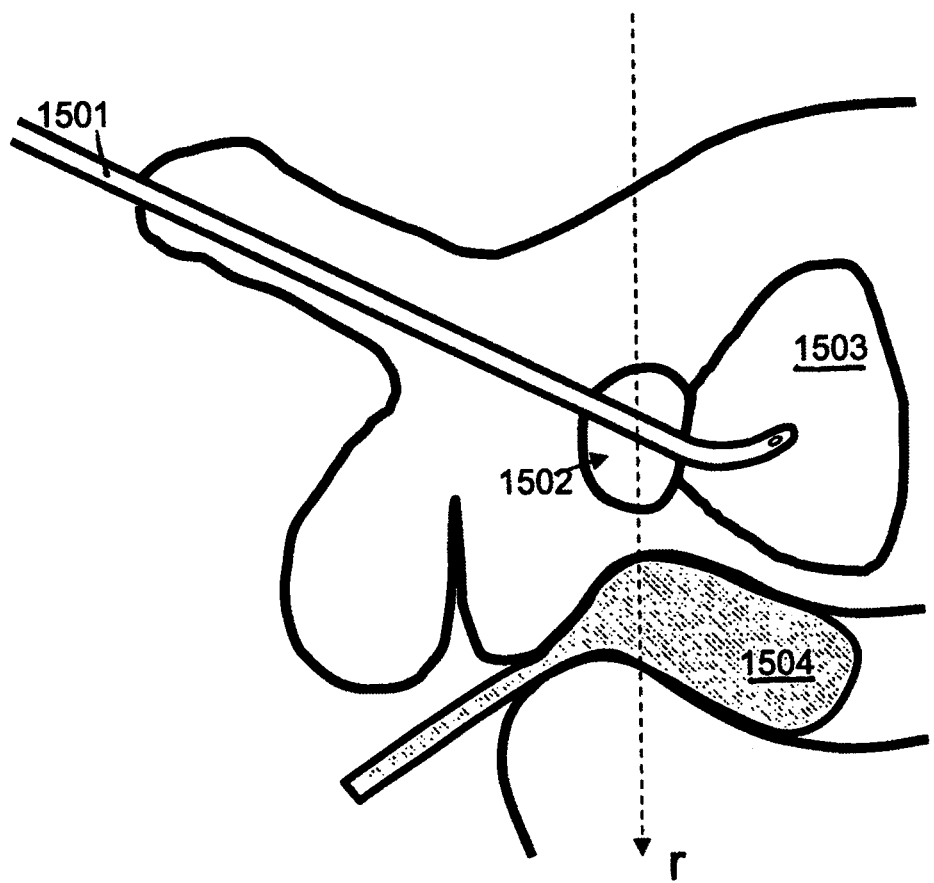
FIG. 15 illustrates a typical prostate thermal therapy arrangement with devices inserted in the urethra and rectum.

Referring to FIG. 15, an exemplary arrangement for prostate thermal therapy with devices employed is shown. A device 1501 is inserted into the urethra (not individually illustrated), passing through the prostate 1502, and into the bladder 1503. Drainage of urine from the bladder 1503 is accomplished by the device 1501 inserted in the bladder 1503. A device 1504 is inserted into the rectum 1505. The devices 1501 and 1504 can be passive (used for cooling/drainage/monitoring), active (delivery of energy for therapy), or both. It will be apparent to those skilled in the art that a multitude of energy sources can be used to generate heating in the prostate including ultrasound, lasers, microwaves, RF, and hot water.

Figure 16:
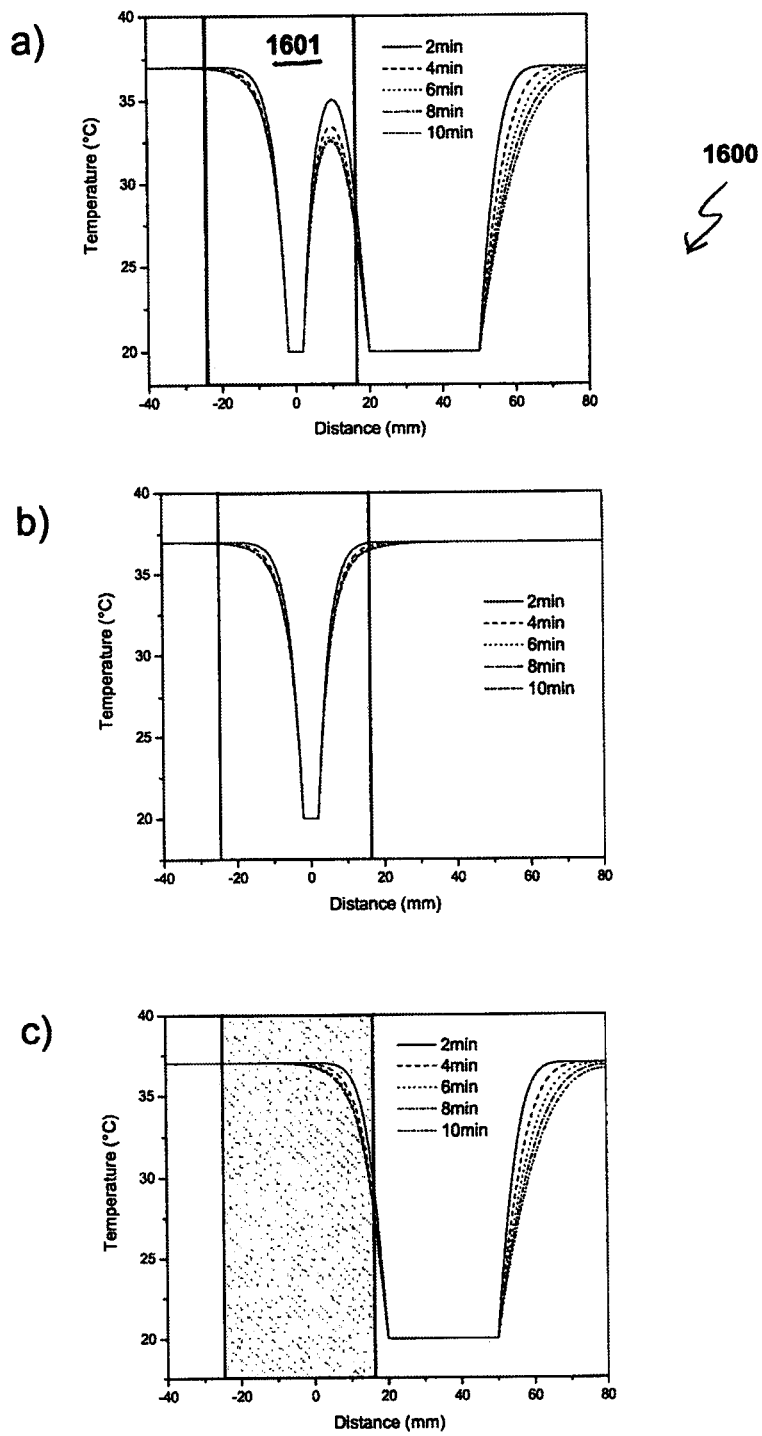
FIGS. 16A-16C are graphical representations illustrating the effect of various cooling arrangements on the baseline temperature in the prostate gland.

Referring also to FIG. 16, a baseline temperature distribution is determined in order to measure the temperature distribution quantitatively. In FIG. 16, thermal modeling is used to predict the baseline temperature distribution arising upon inserting devices into the rectum and/or urethra during prostate thermal therapy. The baseline temperature distribution is determined from the devices 1501 and 1504, for example. The baseline temperature distribution is calculated, for example, using the Bioheat Transfer Equation.

Generally, it is assumed that the body is at 37° C., while the devices are maintained at 20° C. for cooling purposes. The curves 1600 are the temperature profile along the line "r" shown in previous FIG. 15, and the region which falls within the prostate is shown in the hatched lines 1601. The time evolution of the temperature profile 1600 is shown in 2-minute intervals. In the example shown in FIG. 16, a steady-state temperature distribution is reached in approximately 10 minutes. In FIG. 16(a) it was assumed that the rectal space, and the urethra were both cooled by devices held at a temperature of 200C. FIG. 16(b) illustrates the baseline temperature distribution arising from urethral cooling alone, and FIG. 16(c) illustrates the situation with rectal cooling. These are representative examples in a single plane but other situations can also be modeled and compensated in 2 and 3 dimensions. For example, the temperatures of the cooling in the rectum and urethra may be different from each other. FIG. 16 demonstrates the importance of accurately determining the baseline temperature distribution in prostate thermal therapy. Errors up to 10° C. can occur in regions of thermal gradient, which can result in overestimation of the temperature achieved in tissue, and potentially under-treatment due to insufficient heating.

Figure 17:
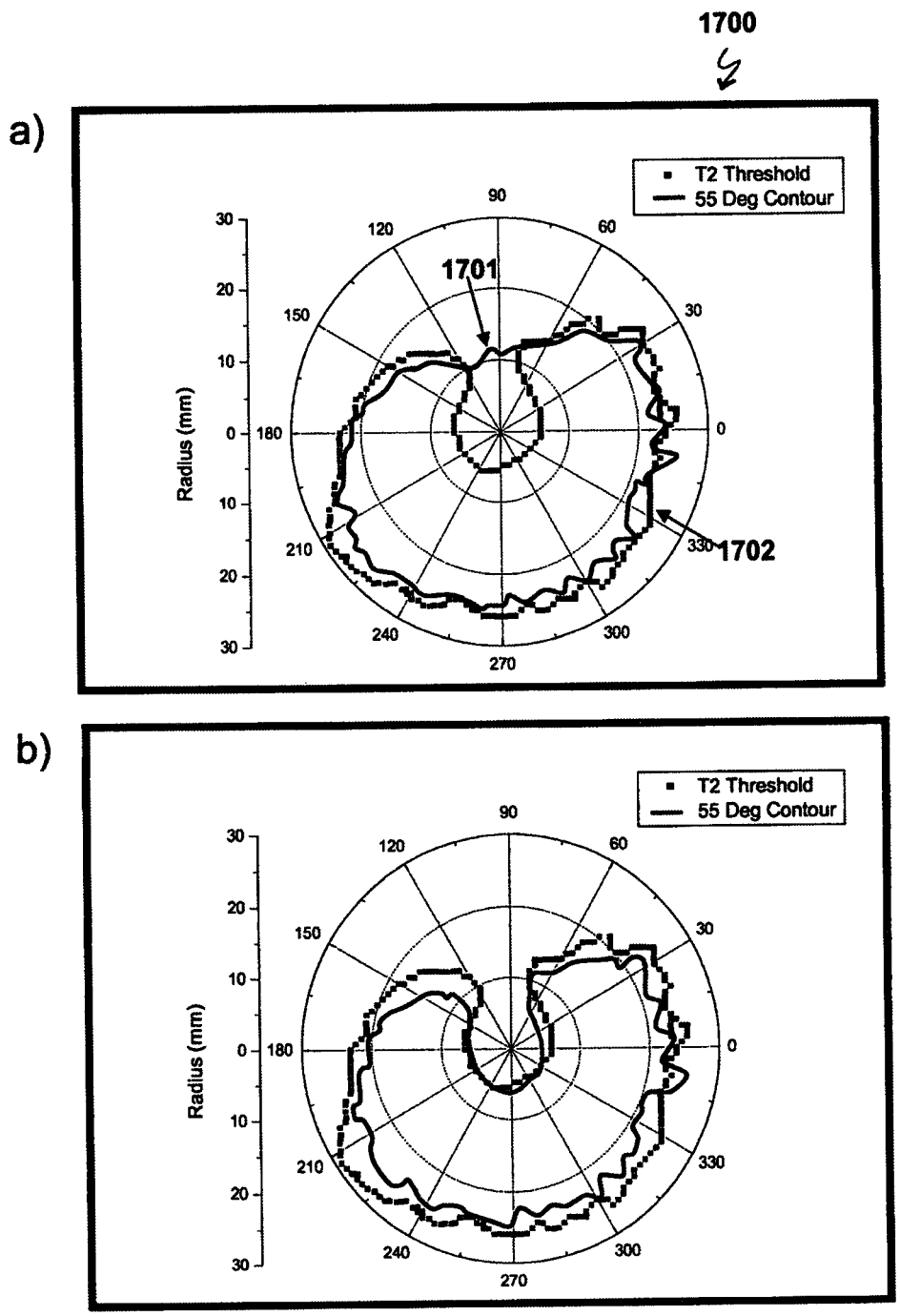
FIGS. 17A-17B are graphical representations illustrating the impact of urethral cooling on the accuracy of temperature estimates during thermal therapy.

The impact of a correction on the measured temperature distribution is shown in FIG. 17, an illustration of the results of an exemplary experiment conducted using a rotating ultrasound heating applicator in a tissue-mimicking gel with MR temperature monitoring. In the experiment, a prostate-shaped heating pattern was delivered in a gel, and confirmation of this treatment was obtained by imaging the gel after heating. The gel material is configured such that it undergoes a large change in T2 upon reaching 55° C., enabling confirmation of the accuracy of the temperature measurements with simple T2-weighted MR images. In FIG. 17(a), a 55° C. contour measured with MRI (solid curve) 1701 is shown, and a pattern of thermal damage in the gel material measured on T2-weighted MR images acquired after the experiment (dotted curve) 1702. Although the 55° C. contour matches the thermal damage pattern well, there is a discrepancy between 60° and 120°, where the thermal damage pattern is close to the device (and the cooling effect is greatest). Referring to FIG. 17(b), the 55° C. contour is corrected for the effect of urethral cooling. The correction was implemented by assuming a baseline temperature distribution similar to that produced in FIG. 16(b). Substantially close agreement between the measured temperature and the actual thermal coagulation can be seen in FIG. 17(b). The utility of compensating for cooling-induced baseline temperature variations during prostate thermal therapy to ensure accurate temperature measurements is shown.

Figure 18:
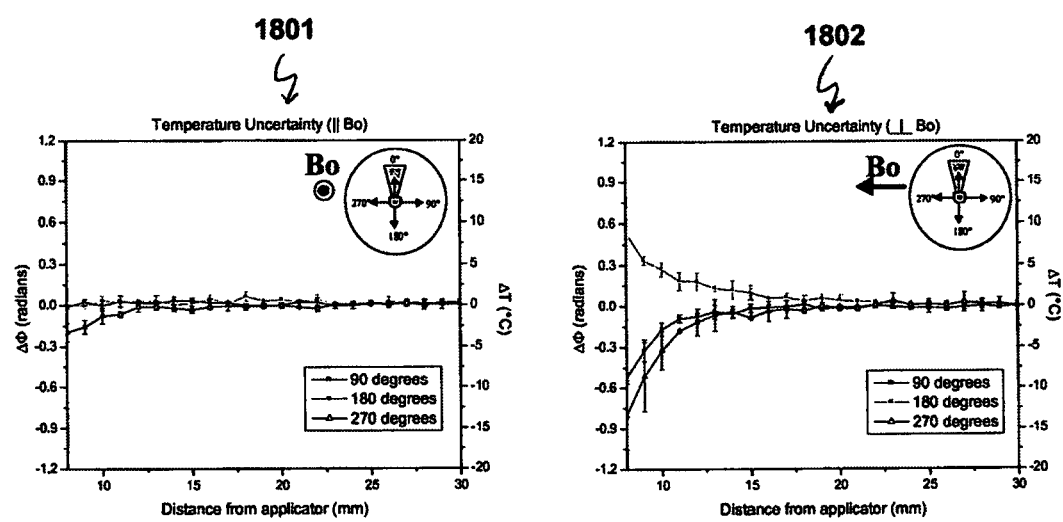
FIGS. 18A-18B are line graphs illustrating the effect of device rotation on the apparent temperature change due to susceptibility artifacts.

Referring also to FIG. 18, the effect of magnetic susceptibility artifacts from a transurethral ultrasound heating applicator rotated through 360° in a phantom is shown. The phase subtraction between two images with the device rotated to different angles results in an apparent temperature change where no energy was delivered, due to changes in the local field after rotating the applicator. It is apparent that this effect is more pronounced when the applicator is oriented perpendicular to the main magnetic field (panel on the right side of the figure) 1802, rather than parallel to it (panel on the left side of the figure) 1801. The effect of the error decreases with distance from the applicator. The susceptibility artefact changes from rotation cannot typically be distinguished from the actual temperature changes measured. Both produce changes in phase from a reference image.

Figure 19:
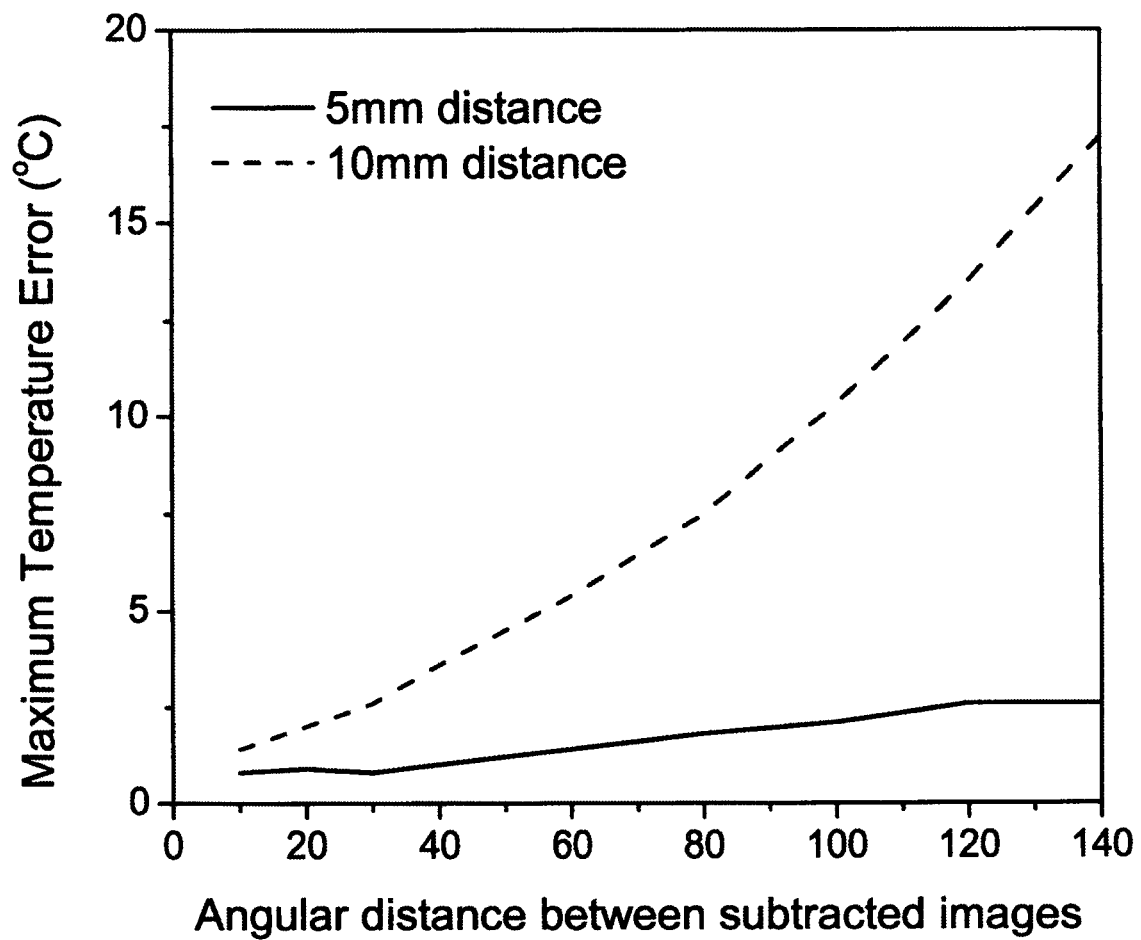
FIG. 19 is a line graph representation of the temperature error that arises and its dependence on the number of reference images acquired.

FIG. 19 shows the capability to correct for this susceptibility artifact by using multiple baselines. In this experiment a heating applicator was rotated 360° in steps of 5°. After each rotation, an image of the phantom containing the applicator was obtained, transverse to the axis of the device. Subtractions were performed between images at increasing angular distance from each other to investigate the importance of using a set of reference images with the correct device position. The graph in FIG. 19 shows the maximum temperature at 5 and 10 mm distance from the device surface as a function of the difference between the position of the device in the two images. As can be seen, the apparent error decreases as the orientations of the device between the images get closer. This figure suggests that a difference of 10° or less is sufficient to reduce this source of error to below 2° C.

The present concepts may be embodied in systems or methods for practicing the concepts described herein and those which become clear to those skilled in the present art, including but not limited to machinery, hardware, software and computer programs, imaging, medical technology, and others.

By way of example, the present disclosure provides inventions useful in thermal imaging and associated medical applications. Specific embodiments use MRI to determine through measurement and correction techniques detailed above ways to produce more accurate temperature maps of regions of tissue. Such accurate temperature maps may be useful for example in the ultrasonic thermal therapy of organs such as the prostate. Having better temperature maps of organs such as the prostate would aid in improved thermal treatment of such organs for diseases such as BPH and cancer. Some of the errors found in conventional thermal mapping that can be corrected for with the present inventions include motion, magnetic susceptibility artefacts, and cooling gradient effects and others.

While a number of advantages and results may be achieved by practicing the inventions disclosed herein, it is not intended that experiments, treatments, or procedures including or relating to the present disclosure be carried out, especially on live patients, without sufficient knowledge, testing, and verification of the efficacy and safety thereof.

We claim:

1. A method for quantitative monitoring of an effect of a thermal treatment of tissue in a target volume to be treated comprising:

inserting a thermal treatment device into a patient's body so that the treatment device is at least partially disposed within the target volume to be treated;

following placing said treatment device in the patient's body, positioning said treatment device at a first position within the target volume, and acquiring a first reference image of the target volume for said first position of the treatment device within the target volume;

positioning said treatment device within said target volume at a second position, and acquiring a second reference image of the target volume for said second position of the treatment device within the target volume;

if further positions of said treatment device are to be employed in said treatment, continuing to set the treatment device to said further positions, and continuing to acquire respective further reference images of the target volume for each of said further positions of the treatment device within the target volume;

following acquisition of all the reference images, determining a quantitatively accurate baseline temperature distribution in said target volume, comprising quantitative temperature measurements to determine a spatial distribution of the baseline temperature in said target volume with the treatment device in the patient's body;

following determining said baseline temperature distribution, positioning said treatment device at said first position, and delivering a thermal treatment from the thermal treatment device to the target volume with the treatment device in the patient's body at said first position within the target volume;

following delivering said thermal treatment to said target volume with the treatment device at said first position, acquiring another image for said first position in said target volume;

performing a phase subtraction between the another image for said first position and the first reference image to determine a change in phase therebetween and to determine a first spatial temperature distribution in the target volume as a result of said delivery of said thermal treatment for said first position, said first spatial temperature distribution indicating a quantitative respective temperature distribution within the target volume;

positioning said treatment device at said second position, and delivering a thermal treatment from the thermal treatment device to the target volume with the treatment device in the patient's body at said second position within the target volume;

following delivering said thermal treatment to said target volume with the treatment device at said second position, acquiring another image for said second position in said target volume;

performing a phase subtraction between the another image for said second position and the second reference image to determine a change in phase therebetween and to determine a second spatial temperature distribution in the target volume as a result of said delivery of said thermal treatment for said second position, said second spatial temperature distribution indicating a quantitative respective temperature distribution within the target volume;

if further positions of said treatment device are to be employed in said treatment, positioning said treatment device at said further positions, and delivering respective thermal treatments from the thermal treatment device to the target volume with the treatment device in the patient's body at said respective further positions within the target volume;

following delivering said respective further thermal treatments, if any, to said target volume with the treatment device at said respective further positions, acquiring further images for said respective further positions in said target volume;

performing respective further phase subtractions between the respective further images for said respective further positions and the corresponding respective further reference images, if any, to determine corresponding respective further changes in phases therebetween; and to determine respective further spatial temperature distributions, if any, in the target volume as a result of said delivery of said thermal treatments for said further positions, said further spatial temperature distributions indicating quantitative respective temperature distributions within the target volume.

2. The method of claim 1, wherein the phase subtractions are used to calculate respective temperature changes using a proton resonant frequency shift relationship.

3. The method of claim 1, further comprising determining a phase change in a untreated tissue that is proximal to the treated target volume.

4. The method of claim 1, further comprising compensating for a drift in a phase of at least one of the reference images.

5. The method of claim 1, further comprising defining a boundary surrounding said target volume.

6. The method of claim 5, wherein the delivering of the thermal treatments comprises heating the tissue at the target volume boundary using said treatment device to a predetermined temperature level.

7. The method of claim 5, wherein monitoring the effect comprises quantitative monitoring of a thermal effect along the boundary surrounding said target volume.

8. The method of claim 7, wherein the thermal effect is a temperature rise.

9. The method of claim 7, wherein the thermal effect is a thermal dose.

10. The method of claim 7, wherein the thermal effect is a maximal temperature.

11. The method of claim 1, wherein the acquiring of the reference images comprises acquiring a magnetic resonance image (MRI) of the target volume.

12. The method of claim 1, wherein delivering the treatment comprises delivering a predetermined thermal dose to the tissue within the target volume.

13. The method of claim 1, wherein the reference images are acquired following an initial preparation of the tissue within the target volume.

14. The method of claim 13, wherein said initial preparation includes a step of application of a pharmaceutical agent to reduce tissue movement within the target volume.

15. The method of claim 13, wherein said initial preparation includes a step of mechanical restraint of the tissue within the target volume to reduce tissue movement within the target volume.

16. The method of claim 1, wherein the steps of acquiring the reference images is followed by a step of stabilizing a temperature of a region of tissue in physical proximity to the treatment device by application of a cooling fluid to cool said region of tissue in conjunction with the thermal treatment.

* * * * *